(12) United States Patent
Robertson et al.

(10) Patent No.: US 11,612,321 B2
(45) Date of Patent: Mar. 28, 2023

(54) TRANSBODY COMMUNICATION SYSTEMS EMPLOYING COMMUNICATION CHANNELS

(71) Applicant: OTSUKA PHARMACEUTICAL CO., LTD., Tokyo (JP)

(72) Inventors: Timothy Robertson, Belmont, CA (US); Kenneth C. Crandall, Sunnyvale, CA (US); Lawrence W. Arne, Redwood City, CA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 404 days.

(21) Appl. No.: 16/789,361

(22) Filed: Feb. 12, 2020

(65) Prior Publication Data

US 2020/0254268 A1    Aug. 13, 2020

Related U.S. Application Data

(63) Continuation of application No. 12/324,798, filed on Nov. 26, 2008, now abandoned.

(60) Provisional application No. 60/990,562, filed on Nov. 27, 2007, provisional application No. 60/990,572, filed on Nov. 27, 2007, provisional application No. 60/990,567, filed on Nov. 27, 2007.

(51) Int. Cl.
| | | |
|---|---|---|
| *A61B 5/00* | (2006.01) | |
| *A61B 5/07* | (2006.01) | |
| *H04B 13/00* | (2006.01) | |
| *A61N 1/372* | (2006.01) | |

(52) U.S. Cl.
CPC ............ *A61B 5/0031* (2013.01); *A61B 5/073* (2013.01); *A61B 5/6861* (2013.01); *H04B 13/005* (2013.01); *A61N 1/37252* (2013.01)

(58) Field of Classification Search
CPC .................................................. A61B 5/0031
See application file for complete search history.

(56) References Cited

U.S. PATENT DOCUMENTS

| | | | |
|---|---|---|---|
| 3,679,480 A | 7/1972 | Brown et al. | |
| 3,893,111 A | 7/1975 | Cotter | |
| 3,944,064 A | 3/1976 | Bashaw | |
| 4,055,178 A | 10/1977 | Harrigan | |
| 4,106,348 A | 8/1978 | Auphan | |

(Continued)

FOREIGN PATENT DOCUMENTS

| | | |
|---|---|---|
| CN | 201076456 | 6/2008 |
| EP | 0344939 | 12/1989 |

(Continued)

OTHER PUBLICATIONS

"Modulation and Deviation" by Dave Platt, AE6EO, Oct. 26, 2007.

(Continued)

*Primary Examiner* — Travis R Hunnings
(74) *Attorney, Agent, or Firm* — Pillsbury Winthrop Shaw Pitmann LLP

(57) ABSTRACT

Transbody communication systems employing communication channels are provided. Various aspects include, for example, an in vivo transmitter to transmit an encoded signal; a transbody functionality module to facilitate communication of the encoded signal; and a receiver to receive the encoded signal. Methods and apparatus are also provided.

20 Claims, 7 Drawing Sheets

(56) References Cited

U.S. PATENT DOCUMENTS

| | | |
|---|---|---|
| 4,331,654 A | 5/1982 | Morris |
| 4,418,697 A | 12/1983 | Tama |
| 4,425,117 A | 1/1984 | Hugemann et al. |
| 4,439,196 A | 3/1984 | Higuchi |
| 4,564,363 A | 1/1986 | Bagnall et al. |
| 4,654,165 A | 3/1987 | Eisenberg |
| 4,681,111 A | 7/1987 | Silvian |
| 4,687,660 A | 8/1987 | Baker et al. |
| 4,725,997 A | 2/1988 | Urquhart et al. |
| 4,793,825 A | 12/1988 | Benjamin et al. |
| 4,809,705 A | 3/1989 | Ascher |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,079,006 A | 1/1992 | Urguhart |
| 5,115,548 A | 5/1992 | Nysten |
| 5,176,626 A | 1/1993 | Soehendra |
| 5,283,136 A | 2/1994 | Peled et al. |
| 5,318,557 A | 6/1994 | Gross |
| 5,395,366 A | 3/1995 | D'Andrea et al. |
| 5,485,841 A | 1/1996 | Watkin et al. |
| 5,596,302 A | 1/1997 | Mastrocola et al. |
| D377,983 S | 2/1997 | Sabri et al. |
| 5,720,771 A | 2/1998 | Snell |
| 5,757,326 A | 5/1998 | Koyama et al. |
| 5,792,048 A | 8/1998 | Schaefer |
| 5,794,124 A | 8/1998 | Ito et al. |
| 5,845,265 A | 12/1998 | Woolston |
| 5,921,925 A | 7/1999 | Cartmell et al. |
| 5,925,030 A | 7/1999 | Gross et al. |
| 5,957,854 A | 9/1999 | Besson |
| 5,963,132 A | 10/1999 | Yoakum et al. |
| 6,023,631 A | 2/2000 | Cartmell et al. |
| 6,042,710 A | 3/2000 | Dubrow |
| 6,083,248 A | 7/2000 | Thompson |
| 6,117,077 A | 9/2000 | Del Mar et al. |
| 6,122,351 A | 9/2000 | Schlueter, Jr. et al. |
| 6,141,592 A | 10/2000 | Pauly |
| 6,204,764 B1 | 3/2001 | Maloney |
| 6,206,702 B1 | 3/2001 | Hayden et al. |
| 6,217,744 B1 | 3/2001 | Crosby |
| 6,275,476 B1 | 8/2001 | Wood |
| 6,285,897 B1 | 9/2001 | Kilcoyne et al. |
| 6,289,238 B1 | 9/2001 | Besson |
| 6,315,719 B1 | 11/2001 | Rode et al. |
| 6,344,824 B1 | 2/2002 | Takasugi et al. |
| 6,366,206 B1 | 4/2002 | Ishikawa et al. |
| 6,380,858 B1 | 4/2002 | Yarin et al. |
| 6,394,953 B1 | 5/2002 | Devlin et al. |
| 6,409,674 B1 | 6/2002 | Brockway et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,453,199 B1 | 9/2002 | Kobozev |
| 6,577,893 B1 | 6/2003 | Besson |
| 6,605,046 B1 | 8/2003 | Del Mar |
| 6,632,175 B1 | 10/2003 | Marshall |
| 6,632,216 B2 | 10/2003 | Houzego et al. |
| 6,654,638 B1 | 11/2003 | Sweeney |
| 6,673,474 B2 | 1/2004 | Yamamoto |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,800,060 B2 | 10/2004 | Marshall |
| 6,822,554 B2 | 11/2004 | Vrijens et al. |
| 6,840,904 B2 | 1/2005 | Goldberg |
| 6,929,636 B1 | 8/2005 | van Alten |
| 7,002,476 B2 | 2/2006 | Rapchak |
| 7,009,634 B2 | 3/2006 | Iddan et al. |
| 7,118,531 B2 | 10/2006 | Krill |
| 7,171,177 B2 | 1/2007 | Park et al. |
| 7,253,716 B2 | 8/2007 | Lovoi et al. |
| 7,317,378 B2 | 1/2008 | Jarvis et al. |
| 7,345,588 B2 | 3/2008 | Gerig |
| 7,382,247 B2 | 6/2008 | Welch et al. |
| 7,382,263 B2 | 6/2008 | Danowski et al. |
| 7,414,534 B1 | 8/2008 | Kroll et al. |
| 7,414,543 B2 | 8/2008 | Rye et al. |
| 7,427,266 B2 | 9/2008 | Ayer et al. |
| 7,616,710 B2 | 11/2009 | Kim et al. |
| 7,673,679 B2 | 3/2010 | Harrison et al. |
| 7,779,614 B1 | 8/2010 | McGonagle et al. |
| 7,796,043 B2 | 9/2010 | Euliano et al. |
| 7,806,852 B1 | 10/2010 | Jursen |
| 7,904,133 B2 | 3/2011 | Gehman et al. |
| D639,437 S | 6/2011 | Bishay et al. |
| 8,025,149 B2 | 9/2011 | Sterry et al. |
| 8,036,731 B2 | 10/2011 | Kimchy et al. |
| 8,123,576 B2 | 2/2012 | Kim |
| 8,180,425 B2 | 5/2012 | Selvitelli et al. |
| 8,200,320 B2 | 6/2012 | Kovacs |
| 8,214,007 B2 | 7/2012 | Baker et al. |
| 8,224,667 B1 | 7/2012 | Miller et al. |
| 8,238,998 B2 | 8/2012 | Park |
| 8,249,686 B2 | 8/2012 | Libbus et al. |
| 8,285,356 B2 | 10/2012 | Bly et al. |
| 8,290,574 B2 | 10/2012 | Felid et al. |
| 8,301,232 B2 | 10/2012 | Albert et al. |
| 8,308,640 B2 | 11/2012 | Baldus et al. |
| 8,315,687 B2 | 11/2012 | Cross et al. |
| 8,369,936 B2 | 2/2013 | Farringdon et al. |
| 8,386,009 B2 | 2/2013 | Lindberg et al. |
| 8,440,274 B2 | 5/2013 | Wang |
| 8,512,241 B2 * | 8/2013 | Bandy .................. G16H 40/67 381/99 |
| 2001/0051766 A1 | 12/2001 | Gazdinski |
| 2001/0056262 A1 | 12/2001 | Cabiri et al. |
| 2002/0002326 A1 | 1/2002 | Causey, III |
| 2002/0026111 A1 | 2/2002 | Ackerman |
| 2002/0077620 A1 | 6/2002 | Sweeney et al. |
| 2002/0193669 A1 | 12/2002 | Glukhovsky |
| 2002/0193846 A1 | 12/2002 | Pool et al. |
| 2003/0017826 A1 | 1/2003 | Fishman |
| 2003/0023150 A1 | 1/2003 | Yokoi et al. |
| 2003/0063522 A1 | 4/2003 | Sagar |
| 2003/0076179 A1 | 4/2003 | Branch et al. |
| 2003/0135128 A1 | 7/2003 | Suftin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreassen et al. |
| 2003/0167000 A1 | 9/2003 | Mullick et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0195403 A1 | 10/2003 | Bemer et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216666 A1 | 11/2003 | Ericson et al. |
| 2003/0229382 A1 | 12/2003 | Sun et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0049245 A1 | 3/2004 | Gass |
| 2004/0073454 A1 | 4/2004 | Urquhart et al. |
| 2004/0082982 A1 | 4/2004 | Gord et al. |
| 2004/0092296 A1 | 5/2004 | Minotani et al. |
| 2004/0111011 A1 | 6/2004 | Uchiyama et al. |
| 2004/0115517 A1 | 6/2004 | Fukuda et al. |
| 2004/0121015 A1 | 6/2004 | Chidlaw et al. |
| 2004/0121292 A1 | 6/2004 | Chung et al. |
| 2004/0122297 A1 | 6/2004 | Stahmann et al. |
| 2004/0122315 A1 | 6/2004 | Krill |
| 2004/0171914 A1 | 9/2004 | Avni |
| 2004/0186365 A1 | 9/2004 | Jin et al. |
| 2004/0193029 A1 | 9/2004 | Chiba |
| 2004/0193446 A1 | 9/2004 | Mayer et al. |
| 2004/0125084 A1 | 10/2004 | Shimizu et al. |
| 2004/0199222 A1 | 10/2004 | Sun et al. |

(56) References Cited

U.S. PATENT DOCUMENTS

| | | |
|---|---|---|
| 2004/0220643 A1 | 11/2004 | Schmidt |
| 2004/0267240 A1 | 12/2004 | Gross et al. |
| 2005/0043634 A1 | 2/2005 | Yokoi et al. |
| 2005/0054897 A1 | 3/2005 | Hashimoto et al. |
| 2005/0055014 A1 | 3/2005 | Coppeta et al. |
| 2005/0075145 A1 | 4/2005 | Dvorak et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0115561 A1 | 6/2005 | Stahmann et al. |
| 2005/0117389 A1 | 6/2005 | Worledge |
| 2005/0131281 A1 | 6/2005 | Ayer et al. |
| 2005/0137480 A1 | 6/2005 | Alll et al. |
| 2005/0143623 A1 | 6/2005 | Kojima |
| 2005/0151625 A1 | 7/2005 | Lai |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0240305 A1 | 10/2005 | Bogash et al. |
| 2005/0245794 A1 | 11/2005 | Dinsmoor |
| 2005/0267756 A1 | 12/2005 | Schultz et al. |
| 2005/0277912 A1 | 12/2005 | John |
| 2005/0277999 A1 | 12/2005 | Strother et al. |
| 2005/0280539 A1 | 12/2005 | Pettus |
| 2005/0288594 A1 | 12/2005 | Lewkowic et al. |
| 2006/0001496 A1 | 1/2006 | Abrosimov et al. |
| 2006/0030760 A1 | 2/2006 | Geiger |
| 2006/0061472 A1 | 3/2006 | Lovoi et al. |
| 2006/0065713 A1 | 3/2006 | Kingery |
| 2006/0078765 A1 | 4/2006 | Yang et al. |
| 2006/0095093 A1 | 5/2006 | Bettesh et al. |
| 2006/0109058 A1 | 5/2006 | Keating |
| 2006/0122667 A1 | 6/2006 | Chavan et al. |
| 2006/0148254 A1 | 7/2006 | McLean |
| 2006/0155174 A1 | 7/2006 | Glukhovsky et al. |
| 2006/0158820 A1 | 7/2006 | Takiguchi |
| 2006/0161225 A1 | 7/2006 | Wolfe |
| 2006/0164213 A1 | 7/2006 | Burghard et al. |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0216603 A1 | 9/2006 | Choi |
| 2006/0229053 A1 | 10/2006 | Sivard |
| 2006/0255064 A1 | 11/2006 | Donaldson |
| 2006/0268546 A1 | 11/2006 | Hoag |
| 2006/0280227 A1 | 12/2006 | Pinkney |
| 2007/0000776 A1 | 1/2007 | Karube et al. |
| 2007/0008113 A1 | 1/2007 | Spoonhower et al. |
| 2007/0049339 A1 | 3/2007 | Barak et al. |
| 2007/0055098 A1 | 3/2007 | Shimizu et al. |
| 2007/0073353 A1 | 3/2007 | Rooney et al. |
| 2007/0123772 A1 | 5/2007 | Euliano et al. |
| 2007/0135691 A1 | 6/2007 | Zingelewicz et al. |
| 2007/0142721 A1 | 6/2007 | Berner et al. |
| 2007/0167495 A1 | 7/2007 | Brown et al. |
| 2007/0167848 A1 | 7/2007 | Kuo et al. |
| 2007/0123659 A1 | 9/2007 | Trovato et al. |
| 2007/0207858 A1 | 9/2007 | Breving |
| 2007/0213659 A1 | 9/2007 | Trovato et al. |
| 2007/0249946 A1 | 10/2007 | Kumar et al. |
| 2007/0255198 A1 | 11/2007 | Leong et al. |
| 2007/0291715 A1 | 12/2007 | Laroia et al. |
| 2008/0015421 A1 | 1/2008 | Penner |
| 2008/0015494 A1 | 1/2008 | Santini et al. |
| 2008/0020037 A1 | 1/2008 | Robertson |
| 2008/0033301 A1 | 2/2008 | Dellavecchia et al. |
| 2008/0065168 A1 | 3/2008 | Bitton et al. |
| 2008/0077028 A1 | 3/2008 | Schaldach et al. |
| 2008/0091089 A1 | 4/2008 | Guillory et al. |
| 2008/0099366 A1 | 5/2008 | Niemie et al. |
| 2008/0114224 A1 | 5/2008 | Bandy et al. |
| 2008/0139907 A1 | 6/2008 | Rao et al. |
| 2008/0146871 A1 | 6/2008 | Arneson et al. |
| 2008/0051767 A1 | 8/2008 | Rossing et al. |
| 2008/0194912 A1 | 8/2008 | Trovato et al. |
| 2008/0223936 A1 | 9/2008 | Mickle et al. |
| 2008/0269664 A1 | 10/2008 | Trovato et al. |
| 2008/0281636 A1 | 11/2008 | Jung et al. |
| 2008/0284599 A1 | 11/2008 | Zdeblick et al. |
| 2008/0288026 A1 | 11/2008 | Cross et al. |
| 2008/0299197 A1 | 12/2008 | Toneguzzo et al. |
| 2008/0306359 A1 | 12/2008 | Wong |
| 2008/0306360 A1 | 12/2008 | Robertson et al. |
| 2008/0316020 A1 | 12/2008 | Robertson et al. |
| 2009/0009332 A1 | 1/2009 | Nunez et al. |
| 2009/0030293 A1 | 1/2009 | Cooper et al. |
| 2009/0062670 A1 | 3/2009 | Sterling |
| 2009/0076340 A1 | 3/2009 | Libbus et al. |
| 2009/0076397 A1 | 3/2009 | Libbus et al. |
| 2009/0105561 A1 | 4/2009 | Boydon et al. |
| 2009/0082645 A1 | 5/2009 | Hafezi et al. |
| 2009/0135886 A1 | 5/2009 | Robertson et al. |
| 2009/0149839 A1 | 6/2009 | Hyde et al. |
| 2009/0192556 A1* | 7/2009 | Wu ................. A61B 5/1116 607/3 |
| 2009/0203964 A1 | 8/2009 | Shimizu et al. |
| 2009/0227204 A1 | 9/2009 | Robertson et al. |
| 2009/0253960 A1 | 10/2009 | Takenaka et al. |
| 2009/0277815 A1 | 11/2009 | Kohl et al. |
| 2009/0292194 A1 | 11/2009 | Libbus et al. |
| 2009/0301925 A1 | 12/2009 | Allara et al. |
| 2010/0006585 A1 | 1/2010 | Flowers et al. |
| 2010/0033324 A1 | 2/2010 | Shimizu et al. |
| 2010/0062709 A1 | 3/2010 | Kato |
| 2010/0063841 A1 | 3/2010 | D'Ambrosia |
| 2010/0069717 A1 | 3/2010 | Hafezi et al. |
| 2010/0139672 A1 | 6/2010 | Kroll et al. |
| 2010/0160742 A1 | 6/2010 | Seidl et al. |
| 2010/0295694 A1 | 11/2010 | Kauffman et al. |
| 2010/0299155 A1 | 11/2010 | Findlay et al. |
| 2010/0312188 A1 | 12/2010 | Robertson et al. |
| 2010/0332443 A1 | 12/2010 | Gartenberg |
| 2011/0009715 A1 | 1/2011 | O'Reilly et al. |
| 2011/0040203 A1 | 2/2011 | Savage et al. |
| 2011/0050431 A1 | 3/2011 | Hood et al. |
| 2011/0054265 A1 | 3/2011 | Hafezi et al. |
| 2011/0144470 A1 | 6/2011 | Mazar et al. |
| 2011/0279963 A1 | 11/2011 | Kumar et al. |
| 2012/0029309 A1 | 2/2012 | Paquet et al. |
| 2012/0089000 A1 | 4/2012 | Bishay et al. |
| 2012/0101396 A1 | 4/2012 | Solosko et al. |
| 2012/0197144 A1 | 8/2012 | Christ et al. |
| 2012/0265544 A1 | 10/2012 | Hwang et al. |
| 2012/0310070 A1 | 12/2012 | Kumar et al. |
| 2012/0316413 A1 | 12/2012 | Liu et al. |
| 2013/0030259 A1 | 1/2013 | Thomsen et al. |
| 2013/0060115 A1 | 3/2013 | Gehman et al. |

FOREIGN PATENT DOCUMENTS

| | | |
|---|---|---|
| EP | 1246356 | 10/2002 |
| EP | 1534054 | 5/2005 |
| EP | 1702553 | 9/2006 |
| GB | 2432862 | 6/2007 |
| IL | 172917 | 6/2010 |
| JP | 05-228128 | 9/1993 |
| JP | H0646539 | 2/1994 |
| JP | 09-330159 | 12/1997 |
| JP | 2000-506410 | 5/2000 |
| JP | 2002291684 | 10/2002 |
| JP | 2004134384 | 4/2004 |
| JP | 2005-073886 | 3/2005 |
| JP | 2006006377 | 1/2006 |
| JP | 2006509574 | 3/2006 |
| JP | 2006-187611 | 7/2006 |
| JP | 2006278091 | 10/2006 |
| JP | 2007159631 | 6/2007 |
| JP | 2007-313340 | 12/2007 |
| JP | 2008011865 | 1/2008 |
| JP | 2008501415 | 1/2008 |
| JP | 2009-061236 | 3/2009 |
| JP | 2002-224053 | 8/2022 |
| JP | 2002263185 | 9/2022 |

(56) References Cited

FOREIGN PATENT DOCUMENTS

| | | |
|---|---|---|
| KR | 20020015907 | 3/2002 |
| KR | 20020061744 | 7/2002 |
| KR | 200609977523 | 7/2006 |
| KR | 927471 | 11/2009 |
| TW | 553735 | 9/2003 |
| TW | 200724094 | 7/2007 |
| WO | 1997039963 | 10/1997 |
| WO | 1988002237 | 4/1998 |
| WO | 1999037290 | 7/1999 |
| WO | 2001/047466 | 7/2001 |
| WO | 2002095351 | 11/2002 |
| WO | 2004059551 | 7/2004 |
| WO | 2004066903 | 8/2004 |
| WO | 2004068748 | 8/2004 |
| WO | 2004075751 | 9/2004 |
| WO | 2005/020023 | 3/2005 |
| WO | 2005082436 | 9/2005 |
| WO | 2006035351 | 4/2006 |
| WO | 2006/055892 | 5/2006 |
| WO | 2006/055956 | 5/2006 |
| WO | 2006046648 | 5/2006 |
| WO | 2006/104843 | 10/2006 |
| WO | 2006/116718 | 11/2006 |
| WO | 2006/127355 | 11/2006 |
| WO | 2006119345 | 11/2006 |
| WO | 2007/001724 | 1/2007 |
| WO | 2007/001742 | 1/2007 |
| WO | 2007/013952 | 2/2007 |
| WO | 2007/014084 | 2/2007 |
| WO | 2007/021496 | 2/2007 |
| WO | 2007/027660 | 3/2007 |
| WO | 2007/028035 | 3/2007 |
| WO | 2007036741 | 4/2007 |
| WO | 2007036746 | 4/2007 |
| WO | 2007067054 | 6/2007 |
| WO | 2007115087 | 10/2007 |
| WO | 2007127945 | 11/2007 |
| WO | 2007130491 | 11/2007 |
| WO | 2007133526 | 11/2007 |
| WO | 2007/149546 | 12/2007 |
| WO | 2008/008281 | 1/2008 |
| WO | 2008012700 | 1/2008 |
| WO | 2008/052136 | 5/2008 |
| WO | 2008/063626 | 5/2008 |
| WO | 2008/066617 | 6/2008 |
| WO | 2008/095183 | 8/2008 |
| WO | 2008/101107 | 8/2008 |
| WO | 2008/112577 | 9/2008 |
| WO | 2008/112578 | 9/2008 |
| WO | 20080120156 | 10/2008 |
| WO | 2008/112577 | 11/2008 |
| WO | 2009001108 | 12/2008 |
| WO | 2010000085 | 1/2010 |
| WO | 2010019778 | 2/2010 |
| WO | 2010057049 | 5/2010 |
| WO | 2010080765 | 7/2010 |
| WO | 2010080843 | 7/2010 |
| WO | 2010115194 | 10/2010 |
| WO | 2010132331 | 11/2010 |
| WO | 2011068963 | 6/2011 |
| WO | 2011133799 | 10/2011 |
| WO | 2011159336 | 12/2011 |
| WO | 2011159337 | 12/2011 |
| WO | 2011159338 | 12/2011 |
| WO | 2011159339 | 12/2011 |
| WO | 2012104657 | 8/2012 |
| WO | 2012158190 | 11/2012 |

OTHER PUBLICATIONS

Winter, J_ et al. "The material properties of gelatin gels"; USA Ballistic Research Laboratories, Mar. (1975), pp. 1-157.

Hotz "The Really Smart Phone" The Wall Street Journal, What They Know (2011 ); 6 pp.; http://online.wsj.com/article/SB 1 00014240527 4870454 7604576263261679848814 .him I?mod=djem TE CH_ I.
Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.
Lin et al., "Do Physiological Data Relate to Traditional Usability Indexes?" Proceedings of OZCHI 2005, Canberra, Australia (2005) 10 pp.
Mandryk et al., "A physiological approach for continuously modeling user emotion in interactive play environments" Proceedings of Measuring Behavior (2008) (Maastrichtm The Netherlandsm Aug. 26-29) 2 pp.
Mandryk et al., "Objectively Evaluating Entertainment Technology" Simon Fraser University; CHI (2004) ACM 1-58113-703-6/04/0004; 2 pp.
Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.
"PALO Bluetooth Baseband" PALO Bluetooth Resource Center (2002) Retrieved from internet Dec. 12, 2012 at URL: http://palowireless.com/bluearticles/baseband.asp; first cited in Office Action dated Jan. 17, 2013 for EP08853901.0.
"Smartlife awarded patent for knitted transducer" Innovation in Textiles News: http://www.innovationintextiles.com/articles/208.php; 2pp. (2009).
Heydari et al., "Analysis of the PLL jitter due to power/ground and substrate noise"; IEEE Transactions on Circuits and Systems (2004) 51(12): 2404-16.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Yang et al., "Fast-switching frequency synthesizer with a discriminator-aided phase detector" IEEE Journal of Solid-State Circuits (2000) 35(10): 1445-52.
Mini Mitter Co, Inc. 51 0(k) Premarket Notification for VitalSense. Apr. 22, 2004.
MacKay et al., Radio telemetering from within the body: Inside information is revealed by tiny transmitters that can be swallowed or implanted in man or animal Science 1961 ; 134(3486):1196-1202.
MacKay et al,. Endoradiosonde. Nature 1957;179(4572):1239-40, 179.
Zworkin, A 'radio pill.' Nature 1957;179:898.
Yao et al., Low Power Digital Communication in Implantable Devices Using Volume Conduction of Biological Tissues. Proceedings of the 28th IEEE, EMBC Annual International Conference 2006 (Aug. 30-Sep. 3); New York, USA.
McKenzie et al., Validation of a new telemetric core temperature monitor. J_ Therm. Biol. 2004 ;29 (7-8 ):605-11.
Ta Tbu L et al., Confidence-based data management for personal area sensor networks. ACM International Conference Proceeding Series 2004;72.
Zimmerman. Personal Area Networks: Near-field intrabody communication. IBM Systems Journal 1996;35 (3-4 ):609-17.
Min I Mitter Co, Inc. 510(k) Premarket Notification Mini-Logger for Diagnostic Spirometer. Sep. 21, 1999.
Philips Respironics. 510(k) Premarket Notification for VitalSense. Apr. 22, 2004.
Mini Mitter Co, Inc. Actiheart. Traditional 510(k) Summary. Sep. 27, 2005.
Mini Mitter Co, Inc. VitalSense—Wireless Vital Signs Monitoring. Temperatures.com Mar. 31, 2009.
Mini Mitter Co, Inc. Noninvasive technology to help your studies succeed. Mini Mitter.com Mar. 31, 2009.

(56) References Cited

OTHER PUBLICATIONS

Barrie, Heidelberg pH capsule gastric analysis. Textbook of Natural Medicine, 1992, Pizzomo, Murray & Barrie.
Carlson et al., Evaluation of a non-invasive respiratory monitoring system for sleeping subjects. Physiological Measurement 1999;20(1):53.
Mojaverian et al., Estimation of gastric residence time of the Heidelberg capsule in humans: effect of varying food composition. Gastroenterology 1985;89(2):392-7.
Xiaoming et al., A telemedicine system for wireless home healthcare based on bluetooth and the internet. Telemedicine Journal and e-health 2004;10(S2):S110-6.

\* cited by examiner

TRANSBODY COMMUNICATION SYSTEMS EMPLOYING COMMUNICATION CHANNELS

CROSS-REFERENCE TO RELATED APPLICATIONS

This application is a continuation application claiming priority under 35 U.S.C. § 120 to U.S. patent application Ser. No. 12/324,798, entitled TRANSBODY COMMUNICATION SYSTEMS EMPLOYING COMMUNICATION CHANNELS, filed on Nov. 26, 2008, which applications claim the benefit under Pursuant to 35 U.S.C. § 119(e) to U.S. Provisional Applications Nos. 60/990,562 filed Nov. 27, 2007; 60/990,567 filed Nov. 27, 2007 and 60/990,572 filed Nov. 27, 2007; which applications are incorporated herein by reference for all purposes.

BACKGROUND

Communications play an important role in today's world. Transbody communications, for example, are finding increasing use in medical applications. The term "transbody communications" generally refers to transmission of a signal from an in vivo location to a receiver location, e.g., a second in vivo location, a receiver location extracorporeally associated with the body, etc.

Communications, however, may be susceptible to errors. In particular, noisy transmission environments may distort and corrupt communication data. The noisy transmission environments include the body. Additionally, communication devices may err in signal generation and measurement related to the communication data.

Further, various devices and combinations of devices may exact high power consumption, resulting in a relatively short life cycle for the devices inside the body. Such a short life cycle may result in replacement surgeries and other inconvenient, expensive, and/or high-risk procedures.

As such, there is a continued need for accurate communications and error-free data provided via long-lasting devices. Of particular interest is development of communications channels that may be readily deployed to reliably communicate information from an in vivo location to a receiver positioned in, or in close physical proximity to, a body.

SUMMARY

The system includes an in vivo transmitter to transmit an encoded signal; a transbody functionality module to facilitate communication of the encoded signal; and a receiver to receive the encoded signal to at least facilitate accurate transbody communications and conserve power consumption. The system may further include at least one of a beacon functionality module, a frequency hopping functionality module, and a collision avoidance functionality module. Related methods and apparatus are also provided.

DETAILED DESCRIPTION

Transbody communication systems employing communication channels are provided. Various aspects facilitate accurate communications in noisy environments as well as provide enhanced power conservation features. More particularly, various aspects may be associated with transbody communication systems, e.g., an in vivo transmitter and a signal receiver (sometimes referred to herein as a "receiver") associated with a body. The receiver may be configured to receive and decode a signal from the in vivo transmitter. Various aspects of the invention are characterized by employing a specific communication channel having transbody functionality, e.g., via a transbody functionality module. Related methods are also provided.

The invention may have broad applicability to medical and non-medical fields. The medical fields include, for example, transbody communications systems associated with various medical and therapeutic devices, e.g., cardiac devices, ingestible devices, etc. The non-medical fields include, for example, body associated devices such as gaming devices incorporating physiologic sensing functionality, etc.

Figure 1:
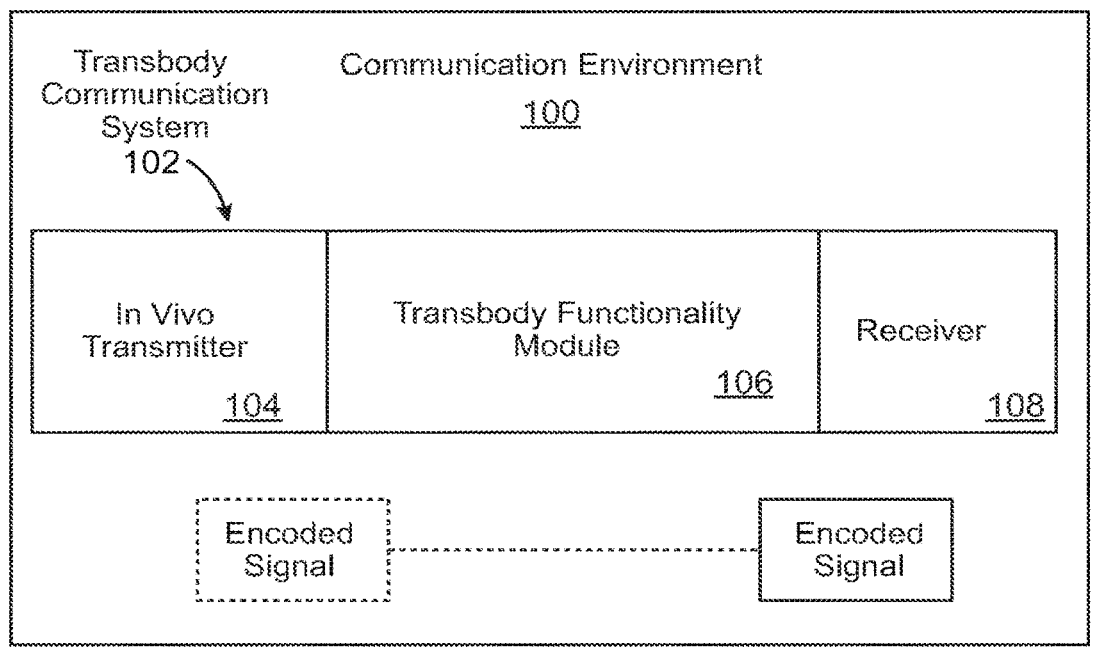
FIG. 1 illustrates a communication environment, including a transbody communication system having a transbody functionality module.

FIG. 1 illustrates a communication environment 100, including a transbody communication system 102. The transbody communication system 102 comprises, for example, an in vivo transmitter 104, a transbody functionality module 106, and a receiver 108. In various aspects, the in vivo transmitter 104 transmits a signal, e.g., an encoded signal, via the transbody communication module 104 to the receiver 108, as hereinafter described in detail.

1.0 In Vivo Transmitter

Implementations of the in vivo transmitter may vary widely. Generally, an in vivo transmitter 102 includes any in vivo device capable of transmitting a signal, e.g., an encoded signal.

In various aspects, the in vivo transmitter 102 may be associated with various devices, e.g., cardiac-related devices, ingestible devices, neural-stimulation related devices, medications, etc. The in vivo transmitter 102, for example, may be wholly or partially integrated with such a device, medication, etc.

One example of such a device is a pharma-informatics enabled pharmaceutical composition, described in PCT Application Serial No. US2006/016370. Another example is an ingestible event marker (IEM) and a personal receiver, described in U.S. Provisional Patent Application Ser. No. 60/949,223. Still another example is a smart parenteral device, described in PCT/US2007/15547. Yet another example is a smart implantable fluid transport device, described in U.S. Provisional Patent Application Ser. No. 60/989,078. Still further examples include implantable physiologic event recorders, described in U.S. Pat. Nos. 5,919,210, 5,989,352, 6,699,200, and 6,895,275; various systems and methods described in PCT application WO2006/116718. Still further examples include PCT application serial Nos. PCT/US2007/022257; PCT/US07/24225; PCT/US08/56296; PCT/US2008/56299 and PCT/US08/77753; and well as U.S. Provisional Application Nos. 61/034,085 and 61/105,346. Each of the foregoing is herein incorporated in its entirety by reference.

The signal transmitted by the device generally includes any signal, data, identifier, representative thereof, etc. Signals include encoded signals, e.g., encode at origin and decoded at destination. Examples of signals include an identifier of a pharmaceutical, a parenteral delivery device, an ingestible event marker, etc., supra.

2.0 Transbody Functionality Module

The signal may be transmitted from the in vivo transmitter 104 via the transbody functionality module 106 to the receiver 108. The transbody functionality module 106 generally uses protocol(s), communication channels, etc., capable of facilitating accurate receipt of signals, data, etc. and/or facilitating low power consumption, Such transbody functionality modules 106 include beacon functionality; frequency hopping functionality, and collision avoidance functionality. Each of the foregoing is discussed in detail hereinafter.

In various aspects, the transbody functionality module 106, and or one or a combination of its submodules (described hereinafter), may be implemented as software, e.g., digital signal processing software; hardware, e.g., a circuit; or combinations thereof.

Communication media for transmission may vary. In one aspect, the body of a patient may be employed as a conduction medium for the signal. As such, the signal is conducted between the in vivo transmitter and the receiver via body fluids, etc. In another aspect, the signal is transmitted via radio frequency (RF) transmission. One skilled in the art will recognize that other communication media are also possible.

Figure 2:
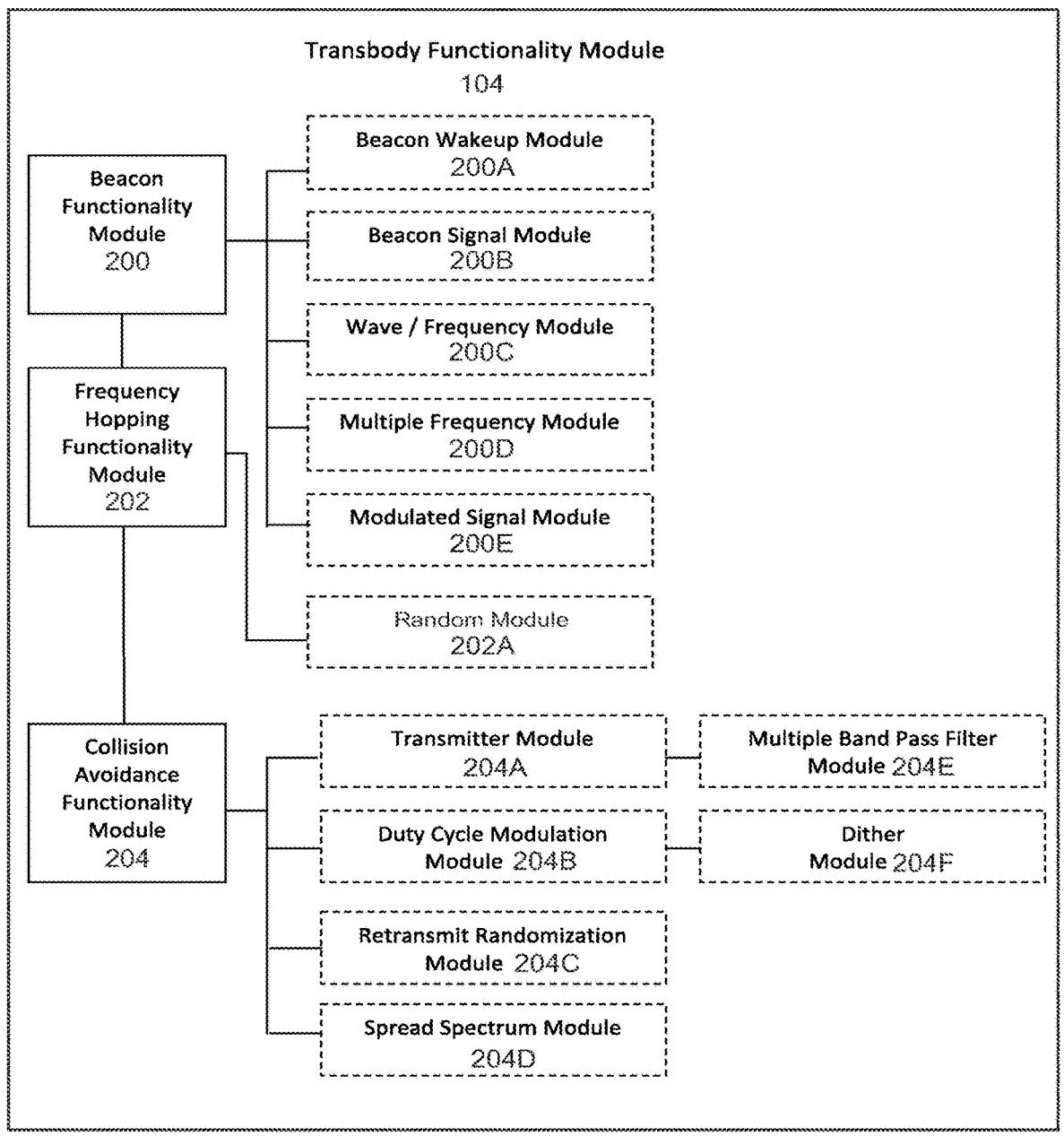
FIG. 2 illustrates the transbody functionality module of FIG. 1 in greater detail.

FIG. 2 illustrates the transbody functionality module 106 of FIG. 1 in greater detail. In various aspects, the transbody functionality modules includes a beacon functionality module 200, a frequency hopping functionality module 202, and a collision avoidance functionality module 204.

2.1 Beacon Functionality Module

Various aspects may employ the beacon functionality module 200. In various aspects, the beacon functionality module 200 may employ one or more of the following: a beacon wakeup module 200A, a beacon signal module 200B, a wave/frequency module 200C, a multiple frequency module 200D, and a modulated signal module 200E.

The beacon functionality module 200 may be associated with beacon communications, e.g., a beacon communication channel, a beacon protocol, etc. For the purpose of the present disclosure, beacons are typically signals sent either as part of a message or to augment a message (sometimes referred to herein as "beacon signals"). The beacons may have well-defined characteristics, such as frequency. Beacons may be detected readily in noisy environments and may be used for a trigger to a sniff circuit, such as those described above.

In one aspect, the beacon functionality module 200 may comprise the beacon wakeup module 200A, having wakeup functionality. Wakeup functionality generally comprises the functionality to operate in high power modes only during specific times, e.g., short periods for specific purposes, e.g., to receive a signal, etc. An important consideration on a receiver portion of a system is that it be of low power. This feature may be advantageous in an implanted receiver, to provide for both small size and to preserve a long-functioning electrical supply from a battery. The beacon wakeup module 200A may enable these advantages by having the receiver operate in a high power mode for very limited periods of time. Short duty cycles of this kind can provide optimal system size and energy draw features.

In practice, the receiver may "wake up" periodically, and at low energy consumption, to perform a "sniff function" via, for example, a sniff circuit. For the purpose of the present application, the term "sniff function" generally refers to a short, low-power function to determine if a transmitter signal is present. If a transmitter signal is detected by the sniff function, the device may transition to a higher power communication decode mode. If a transmitter signal is not present, the receiver may return, e.g., immediately return, to sleep mode. In this manner, energy is conserved during relatively long periods when a transmitter signal is not present, while high-power capabilities remain available for efficient decode mode operations during the relatively few periods when a transmit signal is present.

Several modes, and combination thereof, may be available for operating the sniff circuit. By matching the needs of a particular system to the sniff circuit configuration, an optimized system may be achieved.

Figure 3A:
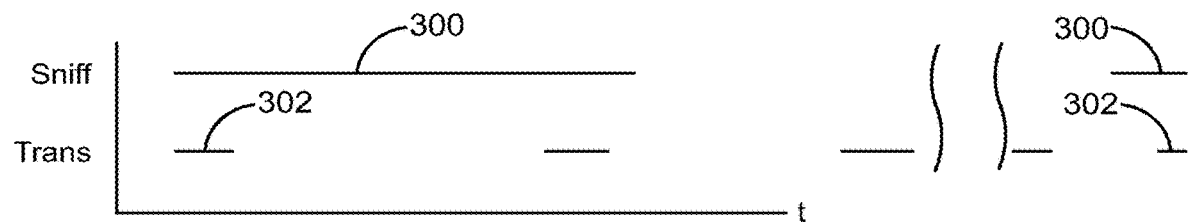
FIG. 3A illustrates a beacon wakeup module providing a sniff period longer than a transmit signal repetition period.

FIG. 3A illustrates the beacon wakeup module 200A wherein a sniff period 300 is longer than a transmit signal repetition period 302. The time function is provided on the x axis. As shown, the transmit signal repeats periodically, with a sniff function also running. In practice, effectively, the sniff period 300 is typically longer than the transmit signal repetition period 302. In various aspects, there may be a relatively a long period of time between the sniff periods. In this way, the sniff function, e.g., implemented as a sniff circuit, is guaranteed to have at least one transmission to occur each time the sniff circuit is active.

Figure 3B:
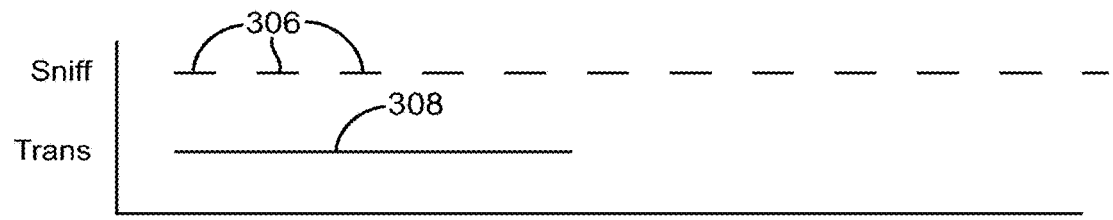
FIG. 3B illustrates a beacon wakeup module providing a short but frequent sniff period and a long transmit packet are provided.

FIG. 3B illustrates the beacon wakeup module 200A wherein a short but frequent sniff period 306 and a long transmit packet 308 are provided. The sniff circuit will activate at some point during the transmit time. In this manner, the sniff circuit may detect the transmit signal and switch into a high power decode mode.

An additional beacon wakeup aspect is to provide the "sniffing" function in a continuous mode. In contrast to the approaches provided above, this aspect of the transbody beacon transmission channel may exploit the fact that the total energy consumption is the product of average power consumption and time. In this aspect, the system may minimize the total energy consumption by having very short periods of activity, in which case the periods of activity are averaged down to a small number. Alternately, a low continuous sniff activity is provided. In this case, the configuration provides a sufficiently low power so that the transmission receiver runs continuously with a total energy consumption at an appropriate level for the parameters of a specific system.

The system may be passive. Two examples of circuit implementations are provided.

Figure 4A:
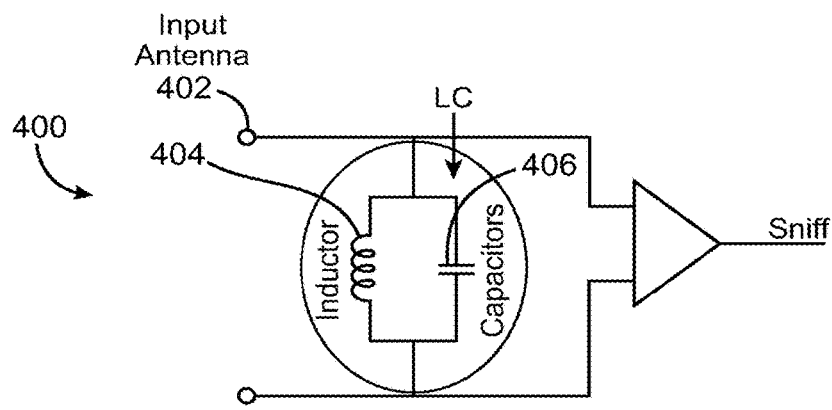
FIG. 4A illustrates a resonant, narrow band analog circuit.

FIG. 4A illustrates a resonant, narrow band analog circuit 400, including input antenna 402, inductor 404, and capacitors 406. In various aspects, the resonant, narrow band analog circuit 400 may have a high impedance. An LC resonator may be provided that is tuned to the frequency of the transmitted signal. The voltage across the LC circuit may be measured, and run into a comparator. When the voltage measurement exceeds a certain value, a gate may be triggered. The circuitry goes then into a high power mode.

Figure 4B:
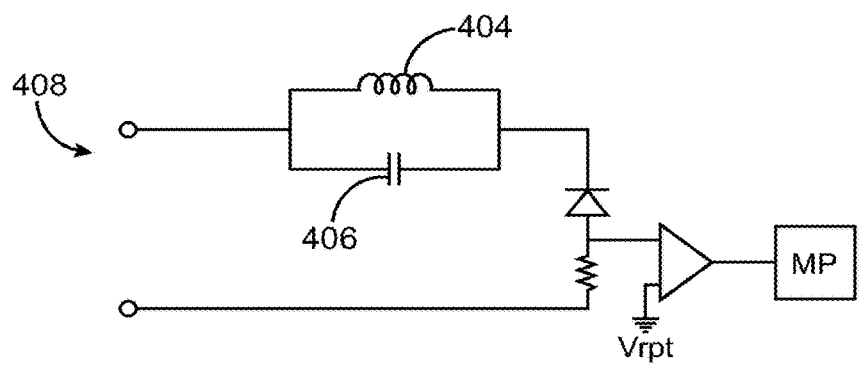
FIG. 4B illustrates classic power detection circuit.

FIG. 4B shows a classic power detect circuit 408. The power detect circuit 408 may be of those known in the art, such as those used in an AM radio to give a light signal that indicates receipt of a radio signal. In one aspect, the power detect circuit 408 is an LC resonant circuit, i.e., a tank circuit. When a signal of the LC resonant frequency is present, the LC tank circuit 'rings up'. Because the circuit has a high Q, its voltage increases dramatically. That voltage is rectified by the diode. When that voltage exceeds a threshold set by Vref, a comparator is triggered. The comparator informs the microprocessor that a signal/circuit is present and directs it to enter the high power mode.

Each of the above-described circuits may be very low powered and may comprise only passive components, with the exception of the comparator. The comparator may also be of very low power. Each circuit may operate continuously. Each circuit may inform the microprocessor when a transmitter is present, e.g., a signal is transmitted, to go into the high power mode. For each of these circuits, a useful prerequisite may be a well defined frequency for the transmitter.

A type of beacon signal associated with the present transbody communication channel is a continuous wave, single frequency tone. In such a case, the continuous single frequency tone triggers either of the circuits in FIG. 4A or 4B, when they are tuned to the correct frequency.

The beacon signal module 200B may provide for beacon signals to be detected digitally, as shown in FIG. 3A or 3B. This may be accomplished by sampling the beacon signals with an A→D converter. The beacon signals are put in a digital processing system. Beacon signals are detected by a single frequency tone which has a very strong characteristic. Examples of such systems are provided in FIG. 5.

Figure 5:
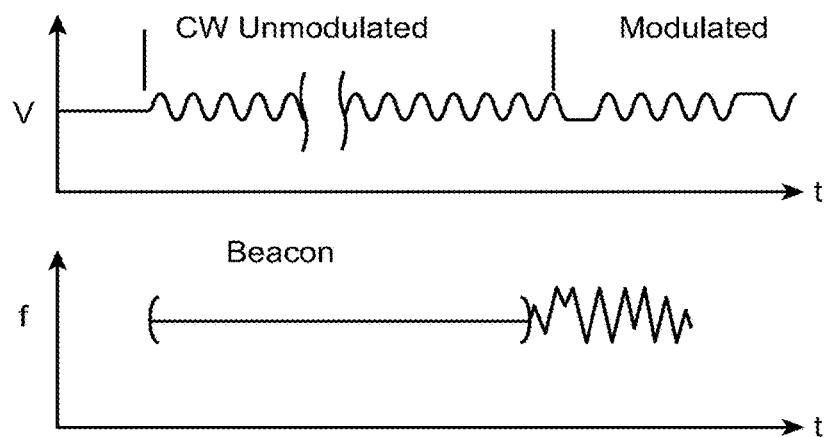
FIG. 5 illustrates beacon functionality having a long period of a continuous wave tone.

FIG. 5 illustrates beacon functionality having a long period of a continuous wave tone, e.g., via the wave/frequency module 200C. In one aspect, the beacon signal consists of a long period of the continuous wave tone. This continuous wave tone has both a modulated portion, which holds the information, and unmodulated portion. In this frequency domain, there is typically a period of well defined frequency. The modulation tends to smear the frequency spectrum. This portion of the wave tone serves as the beacon. It has a single tone in the frequency domain, and is easily recognizable in the spectrogram.

Either of the methods shown previously can detect the single frequency tone. This frequency tone alerts the processing circuitry that a message is coming. It then it moves into decode mode so that the message can be understood. In FIG. 5, this is shown as one packet.

Figure 6:
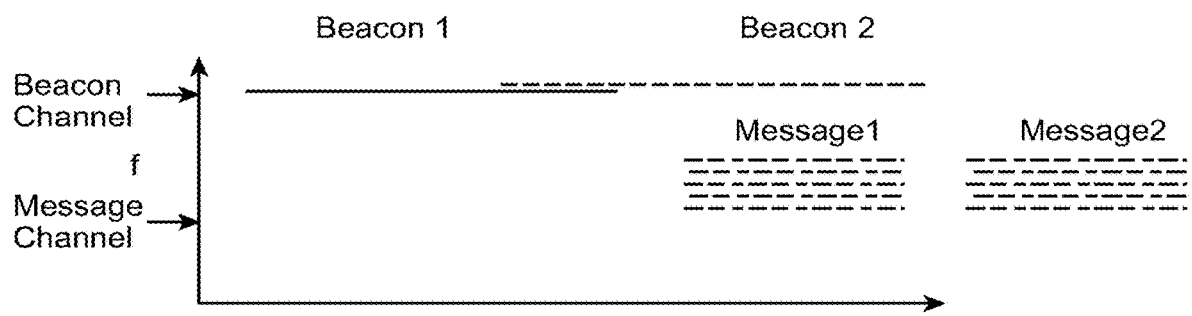
FIG. 6 illustrates a beacon functionality wherein a beacon is associated with one frequency and a message is associated with another frequency.

FIG. 6 illustrates beacon functionality wherein a beacon is associated with one frequency, e.g., a beacon channel, and a message is associated with another frequency, e.g., a message channel. This configuration may be advantageous, for example, when the system is dealing with multiple transmit signals. The solid line represents the beacon from Transmit Signal 1. The dashed line represents the beacon from Transmit Signal 2. In various transmission situations, the Transmit Signal 2's beacon might overlap with that of Transmit Signal 1, as depicted.

Message Signal 1 and Message Signal 2 can be at different frequencies from their respective beacons. One advantage may be that the beacon from Transmit Signal 2 does not interfere with the message from Transmit Signal 1 at all, even though they are transmitted at the same time. By contrast, if an approach were taken in the example shown in FIG. 5, the beacon from the second transmit signal would most likely obscure the message from the first transmit signal.

In this case, the beacon channel is a well defined frequency band. A message is provided in the channel where the data are actually transmitted. Interference between different messages in the message channel can be handled through collision avoidance, described below. While FIG. 6 is shown with two transmitters, it will be apparent to one of ordinary skill in the art to modify the system so as to scale it to many more transmitters. The requirements of a particular system may, to some extent, dictate the particular architecture of that system.

Figure 7:
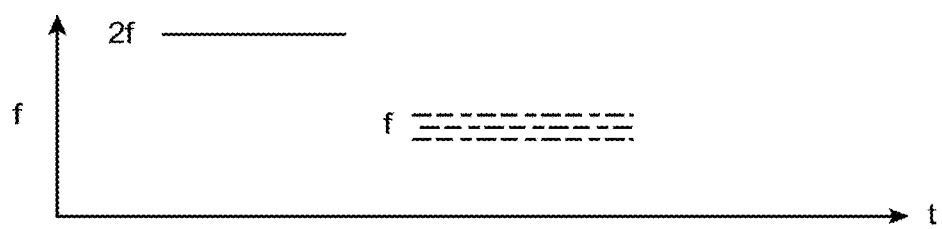
FIG. 7 illustrates a beacon functionality associated with a two-beacon scheme.

FIG. 7 illustrates beacon functionality associated with a two-beacon scheme, e.g., Beacon 1 and Beacon 2. In this case, there is a well-defined mathematical relationship between the frequency of the beacon channel and the frequency of the message channel. If the beacon is a continuous wave signal, or a signal with a very simple modulation, it will be a simple matter to detect the carrier frequency of the beacon signal. In one case, for example, the beacon is at frequency $2f$, and the message is at frequency f, as shown in FIG. 7. In this case, the value of f can be determined from the beacon channel. As a result, if the message is to be demodulated, the frequency is known exactly.

This aspect may be used, inter alia, to address frequency uncertainty. This approach may provide a workable system for message channel modulations which do not have well defined carrier frequencies.

One example of such message channel modulations is spread spectrum modulations. An attempt to determine the frequency of a spread spectrum modulation in and by itself, can be difficult because there is not a well defined peak in the frequency spectrum. However, having the beacon channel accompanying the message channel with a well-defined mathematical relationship allows the message channel frequency to be determined precisely from the beacon channel. The message channel can then be demodulated based on that information.

The above description is of a beacon as a continuous single frequency tone. However, in another aspect, the beacon could have a simple modulation on it. An example of such an aspect is using on-off keying (OOK), or simple frequency modulation. In various aspects, of particular utility is a frequency key shifting (FSK) two tone beacon signal created by two different divide ratios of the master silicon oscillator. This may provide both a unique spectral signature and the frequency ratio of the two tones are invariant to the frequency drift of the silicon oscillator, e.g., an IEM silicon oscillator. The frequency ratio metric may provide a high probability that the signal detected is sourced by the preferred source device, e.g., the IEM. This approach gives the beacon a distinctive signature that is uniquely identifiable from other interferers. In this manner, the system does not risk confusing the beacon with other jammers from the environment. One key characteristic of the frequency is that it stands out as distinctive, and still has a well-defined mathematical relationship in terms of carrier frequency.

Figure 8:
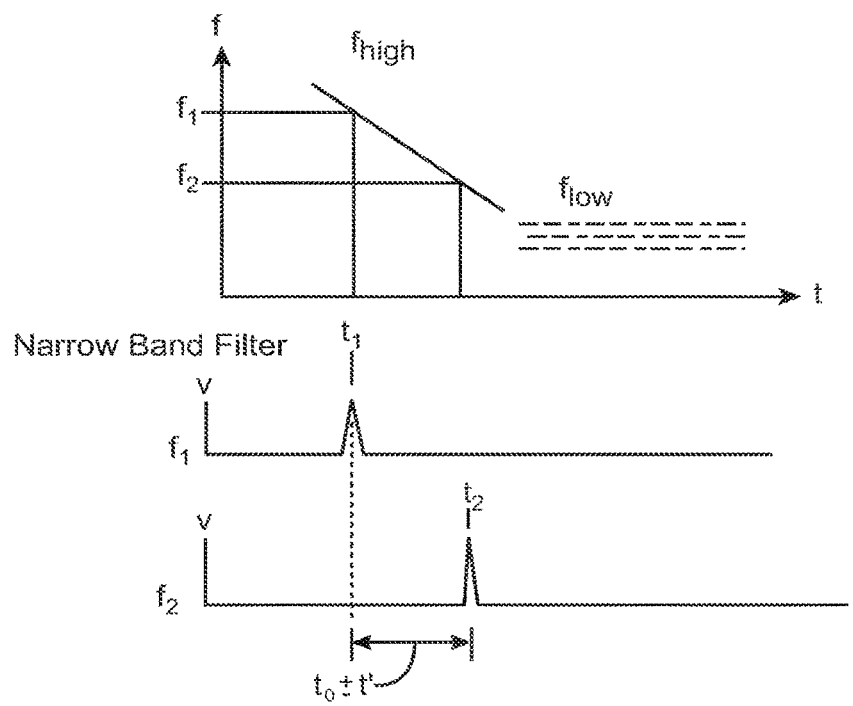
FIG. 8 illustrates a beacon functionality associated with a beacon signal where frequency is a function of time.

FIG. 8 illustrates beacon functionality associated with a beacon signal where frequency is a function of time. One problem that can occur with transmitters is that the carrier frequency is set by a silicon oscillator, and not by a crystal oscillator. This introduces a large uncertainty in characteristic frequency. Determination of that frequency may be a key challenge, both in terms of decoding the packet and detecting the beacon frequency.

The circuits provided in FIGS. 4A and 4B provide an example of this approach. If these circuits have high power (Q), the frequency uncertainty may cause the beacon to fall outside of the response function of the sniff circuits.

Figure 9:
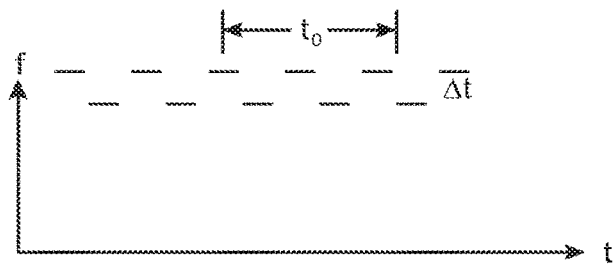
FIG. 9 further illustrates a beacon functionality associated with a beacon signal where frequency is a function of time.

Thus, as illustrated in FIGS. 8 and 9 another type of beacon may be employed. Frequency 700 is ramped over some range, providing a message. Two narrow band filters are provided. The signal is ramped from an $f_{high}$ to an $f_{low}$. Two narrow band filters are tuned to f1 and f2, e.g., via the multiple frequency module 200D. Frequencies f1 and f2 fall between $f_{high}$ and $f_{low}$.

The output of the filter at f1 shows no power, shows a blip in power as the beacon frequency is ramped through f1 at time t1, and then shows no power. Similarly, the output of the filter at f2 would show no power, show a blip in power as the beacon frequency is ramped through f2 at time t2, and then shows no power.

By building a timed-window comparator, an analog sniff circuit is employed which triggers on the time difference between t1 and t2. This can be implemented digitally or in an analog approach. In this case, when the circuit is set on time t1, if time t2 falls within some defined window t0, it indicates that a signal is present.

The ramp is a very distinctive signature. Frequency f1 firing will be detected, and (by example) 10 ms later, f2 firing is detected. If those two events happen within the defined time interval t0, plus or minus t', it indicates that a signal is present. The wakeup circuit is then triggered. The resulting design provides a very low power analog circuit. An important application of the circuit is to determine the frequency as shown in FIG. 8.

The beacon may be modulated to assure that its signature will be distinctive, e.g., via the modulated signal module 200E. One approach to this method is to have the beacon alternate between two frequencies. When this alternation is detected with the well-defined frequency difference and well-defined time period, the confidence level can be very high that a beacon had been detected, rather than some background signal. A similar result can be achieved with on-off keying, in a frequency modulation keying approach.

Any standard modulation technique can be applied to a beacon to give it a distinctive character. In various aspects, data may be imprinted on the beacon, to avoid it being confused with any other signal. In various aspects, the sniff circuit triggers only on the beacon.

There are multiple beacon approaches available to avoid interference. In the idea related to FIG. 6, if there are two beacons transmitting at the same time, transmitter 1 could have beacons at multiple frequencies, e.g., via multiple frequency module 200D, to avoid effects from interference. In a related approach, the aspect is simply to have beacons at different frequencies to avoid contention between the beacons.

In various aspects, a frequency ratio of a beacon and data channel is invariant to frequency error in the ingestible event marker system to provide additional assurance of detection of the encoded signal.

2.2 Frequency Hopping Functionality Module

Various aspects may employ frequency hopping functionality module. The frequency hopping functionality module 202 may be associated with the specific communications channel(s), frequency hopping protocol, etc. As such, various aspects may utilize one or more frequency hopping protocols. For example, the receiver may search the designated range of frequencies in which the transmission could fall. When a single proper decode is achieved, the in vivo transmitter has accomplished its mission of communicating its digital information payload to the receiver.

The transmitted frequency uncertainty provided by random frequency hopping, e.g., via a random module 202A, may create multiple benefits. One such benefit, for example, may be easy implementation on a small die. To illustrate, the in vivo transmitter carrier frequency oscillator can be an inaccurate free running oscillator that is easily implemented on a small portion of a 1 mm die. Accuracies on the order of +/−20 are easily tolerated. This is because the receiver employs frequency searching algorithms.

Another such benefit may be extended battery life. To illustrate, over the course of the transmitter battery life, e.g., three to ten minutes, the probability of the transmitter transmitting on a clear channel that can be received by the frequency agile receiver may be significantly enhanced due to random frequency hopping.

Still another benefit may be minimized collision events in high volume environments. To illustrate, minimization of collision probability when multiple in vivo transmitters, e.g., ingestible event markers, are potentially transmitting simultaneously, such as in instances where the multiple ingestible event markers are ingested concurrently or in close temporal proximity. Stated differently, without frequency hopping functionality, there may be a high probability that ingestible event markers of a similar lot will transmit on the same (or nearly the same) frequency, resulting in multiple collisions.

In certain aspects, the useful frequency spectrum for use in volume conduction applications ranges from about 3 kHz to 150 kHz. Through detailed animal studies it has been observed that in some environments, the in vivo transmitter, supra, having a received signal level in the range of 1 to 100 µV may compete with narrow band interfering signals on the order of hundreds to thousands of µV in the same frequency spectrum. To mitigate the destructive nature of interfering signals, a frequency hopping channel or protocol may be employed in which the in vivo transmitter randomly frequency hops a narrow band transmitted signal, e.g., a modulated signal such as a binary phase shift keying (BPSK) signal or FSK signal, output on each transmission.

2.3 Collision Avoidance Functionality Module

Various aspects may employ a collision avoidance functionality module. The collision avoidance functionality module may be associated with the specific communications channel(s), collision avoidance protocols, etc. As such, various aspects may utilize various collision avoidance protocol techniques associated with the specific communications channel(s). Collision avoidance techniques may be particularly useful, for example, in environments where two or more in vivo transmitters are present, e.g., where an individual ingests multiple IEMs. In such an environment, if the various in vivo transmitters send their signals continuously, the transmission of one may obscure the transmission from all the other in vivo transmitters. As a result, failure to detect signals may increase significantly.

Various aspects may include various collision avoidance approaches, alone or in various combinations.

One such approach employs multiple transmit frequencies. By using frequency-selective filtering, the transmitter broadcasting at f1 can be distinguished from the transmitter broadcasting at f2, even if they are transmitting simultaneously. An alternative to this approach is illustrated in FIG. 9.

Figure 10:
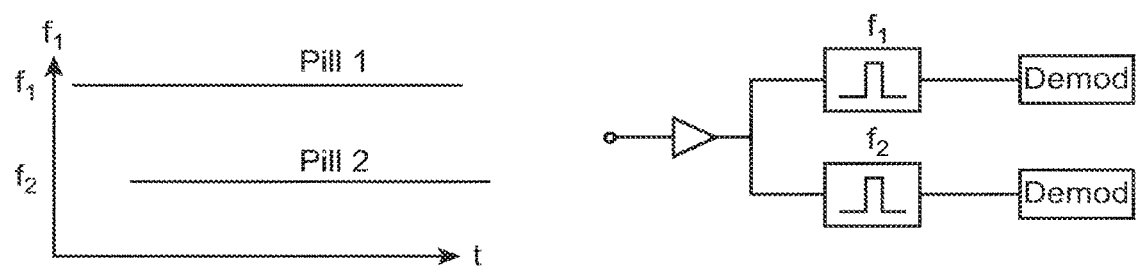
FIG. 10 illustrates a collision avoidance functionality having one collision avoidance technique.

FIG. 10 illustrates a first collision avoidance technique, e.g., via a transmitter module 204A, wherein Transmitter 1 is broadcasting on f1. Transmitter 2 is broadcasting on f2. A receiver and two band pass filters are provided, e.g., via multiple band pass filter module 204E. Band pass filter 1 is sensitive to f1, band pass filter 2 is sensitive to f2. Once signals from the transmitters, e.g., two IEMs associated with Pill 1 and Pill 2, respectively, get through their respective band pass filters, the signals go to demodulators. In various aspects, these demodulators can be implemented as separate analog circuits or in the digital domain. In this manner, collisions may be avoided.

FIGS. 11A-11D illustrate another collision avoidance approach. In various aspects, the specific communications channel(s) may employ duty cycle modulation, e.g., via a duty cycle modulation module 204B, wherein a transmitter need not transmit all the time. If two transmitters, e.g., xmtr1 and xmtr2, are not transmitting simultaneously, they will not interfere with each other. For example, If two transmitters are used which have low duty cycles, such as broadcasting 10% of the time and off 90% of the time, then probabilistically there is only a 20% chance that the signals will overlap with each other. In this manner, collisions may be avoided.

Figure 11A:
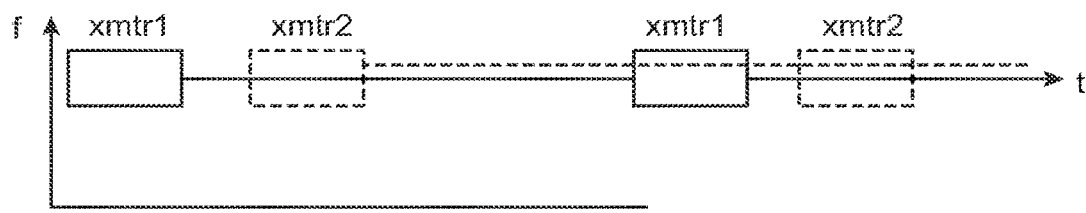
FIGS. 11A-11D illustrate a collision avoidance functionality having another collision avoidance approach.

With reference to FIG. 11A, there a transmitter 1, e.g., xmtr1, that is only on 10% of the time. There is transmitter 2, e.g., xmtr2, that is also only on 10% of the time. Of course, there is some probability that they will transmit simultaneously. However, that probability can be controlled by changing the duty cycle and the frequency spread. As a result, if these two transmit periods are slightly different, they will come in and out of interference with each other. The overlap can be controlled, however, by dithering the duty cycle and the frequency spread, e.g., via dither module 204F and spread spectrum module 204D, respectively. In this manner, otherwise occurring collisions may be avoided.

Figure 11B:
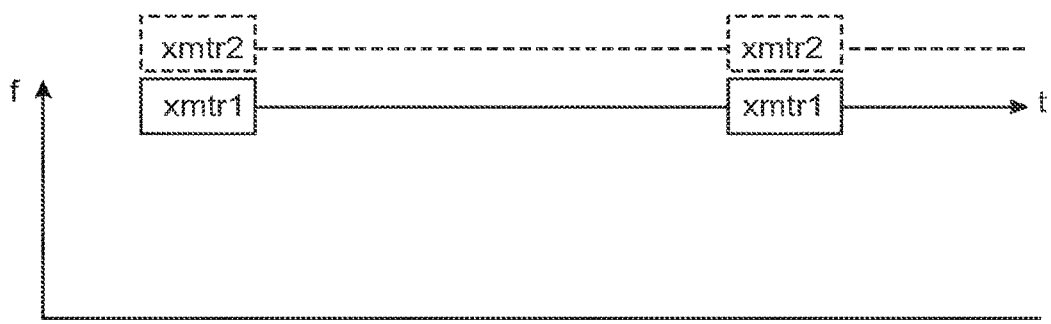

With reference to FIG. 11B, dashed transmitter xmtr2 has a slightly shorter period than the solid transmitter xmtr1. Even though the transmitters begin broadcasting at the same time, after some number of transmissions, the transmitters come out of alignment with each other. As a result, they are now distinct from one another and otherwise occurring collisions may be avoided.

Figure 11C:
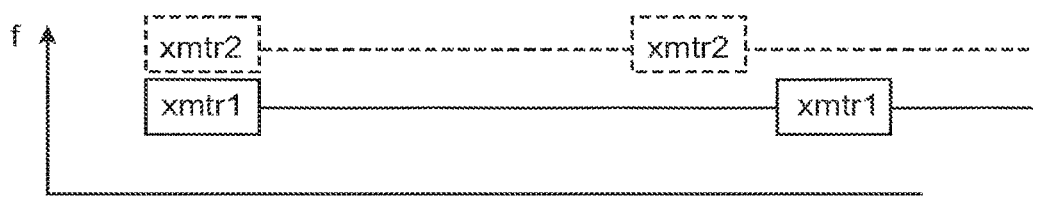

With reference to FIG. 11C, a similar effect can be obtained by having a spread of oscillator frequencies. In practice, the silicon oscillators used for these transmitters have a spread of a few percent in frequency. A 1% difference in frequency means that after a 100 transmissions, two oscillators 1008, 1010 that began in phase with each other are no longer in phase with each other. Various aspects may be based on frequency distribution or the frequencies can also be programmed to be explicitly different, e.g., to have some range of periods. Noise dithering a voltage controlled oscillator frequency can also create this frequency spread.

Figure 11D:
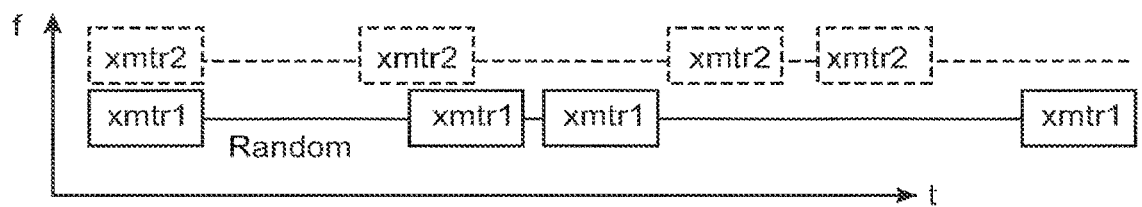

With respect to FIG. 11D, the retry period is randomized. In this example, xmtr1 broadcasts and then waits some random period of time before broadcasting again. The xmtr1 then waits another random period of time before broadcasting again, and so forth. Xmtr2 begins broadcasting at the same time. However, in this case it waits a random time before the next transmission, and waits another random time before the next transmission and so forth. In this way, the probability that two transmitters broadcast simultaneously can be controlled by affecting the standard deviation of the retry periods.

This approach can be based on a pseudo-random sequence that is preprogrammed into the chip. It can also be based on a real physical random number generator (thermal noise), or on the serial number on the chip. Since every transmitter has a unique serial number, some of the lower bits of the serial number can be used to program this randomization time, either directly or by using a linear shift register.

Additional aspects of the transbody transmission channel use spread spectrum transmission to modulate the transmit message. This approach can be direct spread spectrum or frequency hopping spread spectrum. As an example, any of the code division multiple access (CDMA) techniques developed for cell phones that allow for multitudes of cell phones to broadcast on the same frequency without interference can be employed in this aspect. This aspect can also be based on any of the well known codes in spread spectrum, such as Gold Codes or Kasami codes.

The challenge to be addressed is approached probabilistically. A code is selected such that there are sufficiently many that the probability of two transmitters having the same code broadcasting at the same time is sufficiently small. This approach ties into the idea of using a beacon to find the carrier frequency because spread spectrum transmissions in general do not have a well defined carrier frequency. That information is determined, such as from the beacon.

In certain applications, it is useful to combine the different techniques. By example, when there is a long duty cycle, spread spectrum transmission can be particularly valuable. In this case, the probability of a collision happening is the probability of the long duty cycle times the probability of the spread spectrum. There are no restrictions on combining techniques.

In calculations, it is shown that duty cycle works very well for two or three transmitters operating simultaneously. However, in regards to certain applications, the duty cycle method breaks down when there are more than five transmitters providing data in an overlapping time frame.

The most straightforward method to bolster the duty cycle is to add retransmit randomization, e.g., via retransmit randomization module 204C. By adding a few bits of retransmit randomization, the effect is immediately rendered much less pronounced. In this aspect, the system can easily distinguish five to ten simultaneous transmissions.

To get beyond ten transmissions, spread spectrum is one approach of interest. As systems go to many simultaneous transmitters, even if one has a short duty cycle, the total time that multiple transmitters are transmitting becomes a significant portion of the time and collisions become unavoidable.

In systems requiring only a few transmitters, system design can rely on using simpler approaches, such as long duty cycles. Multiple transmit frequencies may be employed in a controlled environment when the frequencies of the transmitters are known. For three to ten transmitters, retransmit randomization works well. Beyond ten transmitters, spread spectrum is one approach that may be employed, and it can combine spread spectrum with other techniques.

Plots on long duty cycle show with three simultaneous transmitters there is about a 1% chance of a transmitter not being detected because of a collision. This is during a one minute transmit interval. One important feature of some transmitters systems is that the transmitters have a finite lifetime. In systems where transmitters have very long lifetimes, these concerns may be absent.

For other kinds of implanted sensors, these are still very important considerations for power consumption. If the system must wait an hour before a window clear enough to transmit a signal is available, then the transmitter is using power all that time.

Another possibility opens up when systems have more sophisticated transmitters. The transmitter can listen for a quiet channel, for example, waiting until it hears nothing transmitting and then transmit.

The spread spectrum approach is quantifiable, depending on how many distinct codes are used. When the Kasami set of codes are used there are 32,000 distinct codes. In this case the probability of having two transmitters transmit on the same code is $1/(32,000)^2$. That probability goes up geometrically with the number of transmitters. Even doing nothing to select transmitters that have distinct codes, and relying on the randomization of code selection, it supports tens, if not hundreds, of transmitters.

Figure 12A:
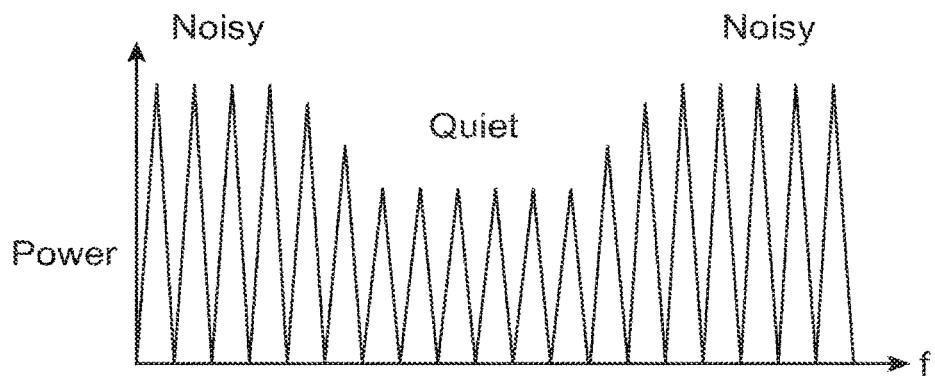
FIGS. 12A and 12B illustrate a collision avoidance functionality having a technique to detect a low amplitude signal in a noisy environment.

In certain aspects, receivers of the system are configured to selectively receive a signal in a quiet part of a given spectrum. FIG. 12A shows an aspect addressing the problem of detecting a low amplitude signal in a noisy environment. One approach to that problem is to find a quiet place in the noise spectrum. The detector of the receiver is programmed to that frequency band. The transmitter periodically broadcasts in that frequency band.

Figure 12B:
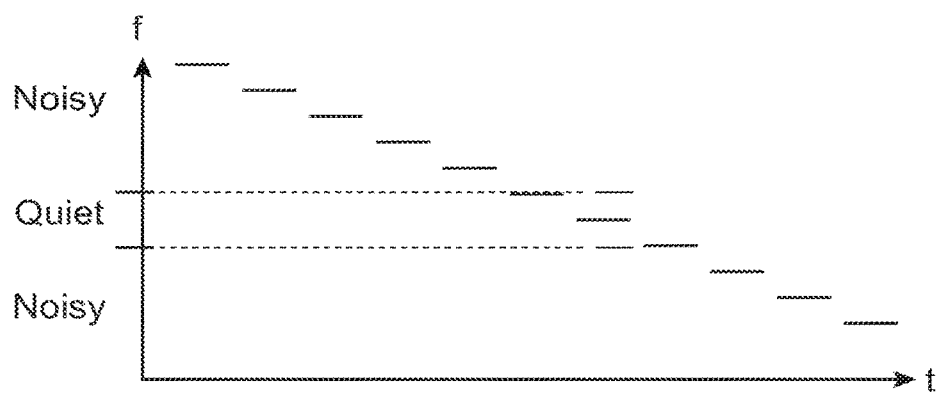

FIGS. 12A and 12B illustrate a technique to detect a low amplitude signal in a noisy environment. With reference to FIG. 12A, in the case where the receiver surveys the noise spectrum, power is a function of frequency. There is a noisy region, quiet region, followed by a noisy region. The broadcast is provided in the quiet region because the least amount of interference is in that region.

In FIG. 12B, the transmission occurs at multiple different frequencies, e.g., a ramping scheme. In various aspects, other schemes may be used such as frequency hopping or random scheme. Typically, the chosen scheme will densely cover the frequency band of interest. In practice, the transmitter will eventually jump into the quiet band and eventually transmit in the quiet band. By having the receiver listen only in that quiet band, there is a good chance of receiving/decoding that signal due to the excellent signal to noise ratio (SNR).

The above configuration in which the receiver is employed to receive only a quiet band is not limited to systems having a collision avoidance channel, as described elsewhere in this application. Instead, receivers as described in any of the following applications may be configured to receive only a quiet channel: PCT application serial no. US2007/024225 titled "Active Signal Processing Personal Health Signal Receivers," and filed on Nov. 19, 2007; WO 2006/116718; 60/866,581; 60/945,251; 60/956,694, 60/887,780 and 2006/116,718; the disclosures of which applications are herein incorporated by reference.

To illustrate some of the foregoing concepts, in one aspect transmissions are broken into two channels. The first channel is used to broadcast the data. A one to two percent duty cycle is performed. Immunity to collisions is enhanced by randomizing the re-broadcast rate. The second channel is used to broadcast a wakeup beacon. A one to two percent duty cycle is performed. The packet rate is in the 10 mSec range. The beacon transmissions are short, in the range of 100 to 200 uSec, when collisions are not of concern. The beacon and data channel carriers are generated from the same oscillator, so from the beacon the data carrier can be calculated. The receiver will turn on every 10 to 30 seconds for a 10 mSec duration. If a beacon is observed, the receiver will stay on to perform a full demodulation and decode. Otherwise, the receiver will return to sleep.

In certain aspects, the above system is modified to include a frequency dither to the packet interval dither.

In certain aspects, the above system is modified to include a longer duration transmission of 16 carrier cycles at 25 kHz (640 uS) with a 1 to 2 percent duty cycle. This complies with narrow band filter compatibility.

In certain aspects, the above system is modified to so that the modulation as BPSK on OOK on the lower channel.

In certain aspects, the above system is modified so that the modulation as OOK burst on the higher beacon channel.

In certain aspects, the above system is modified so that the use of simple multidimensional parity check codes for FEC (forward error correction).

3.0 Receiver

The signal receiver, sometimes referred to herein as the "receiver", generally includes any device or component capable of receiving the signal, e.g., conductively receiving a signal, via one or more specific communication channels.

One example of such a receiver is the personal receiver, supra. Another example of the receiver described in the in: PCT application serial no. PCT/US2006/016370 published as WO 2006/116718; PCT application serial No. PCT/2007/24225 published as WO 2008/063626; PCT application serial no. PCT/US2008/52845 published as US2008/052845; the disclosures of which applications are herein incorporated by reference.

Various aspects include mobile configurations of the receiver that are sized to be stably associated with a living subject in a manner that does not substantially impact movement of said living subject. In certain aspects, the receiver has a small size. To illustrate, the receiver may occupy a volume of space of about five $cm^3$ or fewer, such as about three $cm^3$ or fewer, including about one $cm^3$ or less. In certain aspects, the receiver has a chip size approximately ranging from ten $mm^2$ to two $cm^2$.

The receivers of interest may include both external and implantable receivers.

3.1 External Receivers

In external aspects, the receiver may be ex vivo, i.e., present outside of the body during use. External receiver may be configured in any convenient manner. For example, in certain aspects the externals receivers may be configured to be associated with a desirable skin location. As such, in aspects the external receivers may be configured to contact a topical skin location of a subject. Configurations of interest include, but are not limited to: patches, wrist bands, belts, etc. For instance, a watch or belt worn externally and equipped with suitable receiving electrodes can be used as receivers in accordance with one aspect of the present invention. The receivers may provide a further communication path via which collected data can be extracted by a patient or health care practitioner. For instance, an implanted collector may include conventional RF circuitry operating, e.g., in the 405-MHz medical device band, with which a practitioner can communicate. The practitioner may communicate, for example, via a data retrieval device, such as a wand, etc.

Where the receiver includes an external component, that component may have output devices for providing data, e.g., audio and/or visual feedback. Examples include audible alarms, LEDs, display screens, or the like. The external component may also include an interface port via which the component can be connected to a computer for reading out data stored therein. By further example, the device may be positioned by a harness that is worn outside the body and has one or more electrodes that attach to the skin at different locations.

In certain external aspects, the receiver may be configured to be in contact with or associated with a patient only temporarily, i.e., transiently. For example, the receiver may be associated/attached/in contact while the pill, ingestible event marker, etc., is actually being ingested.

To illustrate, the receiver may be configured as an external device having two finger electrodes or handgrips. Upon ingestion of a pharma-informatics enabled pill, the patient touches the electrodes or grabs the handgrips to complete a conductive circuit with the receiver. Upon emission of the signal from the pill, e.g., when the pill dissolves in the stomach, the signal emitted by the identifier of the pill is picked up by the receiver.

In certain aspects, the external receiver may include miniaturized electronics which are integrated with the electrodes to form a bandage-style patch with electrodes that, when applied, contact the skin. The bandage-style may be removably attachable, e.g., via an adhesive layer or other construction. A battery and electronics may also be included. The bandage-style patch may be configured to be positioned on a desirable target skin site of the subject, e.g., on the chest, back, side of the torso, etc. In these aspects, the bandage circuitry may be configured to receive signals from devices inside of the subject, e.g., from an identifier of a pharma-informatics enabled pharmaceutical composition, and then relay this information to an external processing device, e.g., a PDA, smartphone, mobile phone, handheld device, computer, etc., as described in greater detail elsewhere. Bandage-style devices that may be readily adapted for use in the present systems include, but are not limited to, those described in U.S. Pat. No. 6,315,719 and the like, the disclosures of which are herein incorporated by reference.

3.2 Implantable Receivers

In certain aspects, the receiver may be an implantable, i.e., designed and/or configured for implantation into a subject. Implantation may be on a temporary basis or a permanent basis. In these aspects, the receiver is in vivo during use. Generally, implantable receivers may maintain functionality when present in a physiological environment, including a high salt, high humidity environment found inside of a body, for various periods of time. Periods of time, for example, include a few minutes to eighty years. More specific time periods include, for example, one or more hours, one or more days, one or more weeks, one or more months, and one or more years.

For implantable aspects, the receiver may have any convenient shape, including but not limited to: capsule-shaped, disc-shaped, etc. Various receivers may have relatively small sizes. These small sizes may be achieved, for example, by incorporation of a rechargeable battery. In one aspect, the rechargeable battery has a life span of about two weeks. In another aspect, the rechargeable battery automatically charges from various sources, e.g., coils in the patient's bed. The receiver may be configured to be placed in a number of different locations. Examples of locations include the abdomen, the small of the back, the shoulder, e.g., where implantable pulse generators are placed, etc.

In certain implantable aspects, the receiver is a standalone device, i.e., not physically connected to any other type of implantable device. In yet other aspects, the receiver may be physically coupled to a second implantable device, e.g., a device which serves as a platform for one or more physiological sensors. Such a device may be a lead, such as a cardiovascular lead. To illustrate, the cardiovascular lead may include one or more distinct physiological sensors, e.g., where the lead is a multi-sensor lead (MSL). Implantable devices of interest further include, but are not limited to: implantable pulse generators, neurostimulator devices, implantable loop recorders, etc.

Receivers may further include a receiver element which serves to receive the signal of interest. The receiver may include a variety of different types of receiver elements, where the nature of the receiver element necessarily varies depending on the nature of the signal produced by the signal generation element. In certain aspects, the receiver may include one or more electrodes for detecting signal emitted by the signal generation element. To illustrate, the receiver device may be provided with two electrodes that are dispersed at a predetermined distance. The predetermined distance may allow the electrodes to detect a differential voltage. The distance may vary, and in certain aspects, ranges from about 0.1 to about five cm, such as from about 0.5 to about 2.5 cm, e.g., about one cm. In certain aspects, the first electrode is in contact with an electrically conductive body element, e.g., blood, and the second electrode is in contact with an electrically insulative body element relative to said conductive body element, e.g., adipose tissue (fat). In an alternative aspect, a receiver that utilizes a single electrode is employed. In certain aspects, the signal detection component may include one or more coils for detecting a signal emitted by the signal generation element. In certain aspects, the signal detection component includes an acoustic detection element for detecting signal emitted by the signal generation element.

A receiver may handle received data in various ways. In some aspects, the receiver simply retransmits the data to an external device, e.g., via conventional RF communication. In other aspects, the receiver processes the received data to determine whether to take some action such as operating an effector that is under its control, activating a visible or audible alarm, transmitting a control signal to an effector located elsewhere in the body, or the like. In still other aspects, the receiver stores the received data for subsequent retransmission to another device or for use in processing of subsequent data, e.g., detecting a change in some parameter over time. The receivers may perform any combination of these and/or other operations using received data.

In certain aspects, the data that are recorded on the data storage element include at least one of, if not all of, time, date, and an identifier, e.g., global unique serial number, of each composition administered to a patient. The identifier may be the common name of the composition or a coded version thereof. The data recorded on the data storage element of the receiver may further include medical record information of the subject with which the receiver is associated, e.g., identifying information, such as but not limited to name, age, treatment record, etc. In certain aspects, the data of interest include hemodynamic measurements. In certain aspects, the data of interest include cardiac tissue properties. In certain aspects, the data of interest include various physiologic metrics or parameters, e.g., pressure or volume measurements, temperature, activity, respiration rate, pH, etc.

As summarized above, the receivers can be configured to have a very small size. In certain aspects, the desired functionality of the receiver is achieved with one or more integrated circuits and a battery. Aspects of the invention include receivers that have at least a receiver element, e.g., the form of one or more electrodes (such as two spaced apart electrodes) and a power generation element, e.g., a battery, where the battery may be rechargeable, etc., as mentioned above. As such, in certain aspects the power generation element is converted to receive power wirelessly from an external location.

Additional elements that may be present in the receiver include, but are not limited to: a signal demodulator, e.g., for decoding the signal emitted from the pharma-informatics enabled identifier; a signal transmitter, e.g., for sending a signal from the receiver to an external location; a data storage element, e.g., for storing data regarding a received signal, physiological parameter data, medical record data, etc.; a clock element, e.g., for associating a specific time with an event, such as receipt of a signal; a pre-amplifier; a microprocessor, e.g., for coordinating one or more of the different functionalities of the receiver.

Aspects of implantable versions of the receiver will have a biologically compatible enclosure, two or more sense electrodes, a power source, which could either be a primary cell or rechargeable battery, or one that is powered by broadcast inductively to a coil. The receiver may also have circuitry consisting of: a demodulator to decode the transmitted signal, some storage to record events, a clock, and a way to transmit outside the body. The clock and transmit functionality may, in certain aspects, be omitted. The transmitter could be an RF link or conductive link to move information from local data storage to external data storage.

For the external receivers, aspects include structures that have electrodes opposed to the skin, the demodulator, storage, and power. The communication may be wireless or performed over one or more conductive media, e.g., wires, optical fibers, etc.

In certain aspects, the same electrodes are used for receiving and transmitting signals. One mode may be a wristwatch which is conductively in contact with the body. To move the data from the implant to the wristwatch, currents may be sent out the pads and received by the wristwatch. There are a number of RF techniques for facilitating transmission out of the body that may be employed, such as inductive protocols that use coils. Alternatively, electric fields may be employed, using insulated electrodes, for example.

In certain aspects, the components or functional blocks of the present receivers are present on integrated circuits, where the integrated circuits include a number of distinct functional blocks, i.e., modules. Within a given receiver, at least some of, e.g., two or more, up to an including all of, the functional blocks may be present in a single integrated circuit in the receiver. By single integrated circuit is meant a single circuit structure that includes all of the different functional blocks. As such, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain aspects of the present invention may be hybrid integrated circuits, which are miniaturized electronic circuits constructed of individual semiconductor devices, as well as passive components, bonded to a substrate or circuit board.

As reviewed above, the receivers exhibit reliable decoding of an encoded signal even in the presence of substantial noise and a low SNR. This functional aspect of the receivers of the invention may be provided via various schemes. Some such schemes include, for example, coherent demodulation, e.g., Costas loop demodulation, accurate low overhead iterative decoding, Forward Error Correction (FEC), and noise cancellation, e.g., as described in PCT application serial no. PCT/US2007/024225 titled "Active Signal Processing Personal Health Receivers," and filed on Nov. 19, 2007; the disclosure of which is herein incorporated by reference. Other receivers of interest include, but are not limited to, those described in: WO 2006/116718; 60/866,581; 60/945,251; 60/956,694, 60/887,780 and WO 2006/116718; the disclosures of which are herein incorporated by reference.

Methods

Various aspects include, for example, transmitting, via an in vivo transmitter, an encoded signal; facilitating, via a transbody functionality module, communication of the signal; and receiving, via a receiver, the encoded signal, as heretofore described.

In one aspect, the method provides characteristics of the encoded signal, wherein the characteristics optimize power consumption to facilitate the receiver in at least one of the following: spending maximum time in an inactive mode, waking up quickly, and waking up during a period of high probability that the transmitter is present.

Further, various aspects may alternatively or optionally include such steps related to beacon functionality such as facilitating, via a beacon functionality module, communication of the encoded signal; facilitating, via a frequency hopping functionality module, communication of the encoded signal; and facilitating, via a collision avoidance functionality module, communication of the encoded signal. Some functionality may include, for example, providing beacon wakeup functionality; providing beacon signal functionality; generating a continuous wave, single frequency tone; providing a first frequency that is different from a data signal which is at a second frequency; and modulating the encoded signal.

Still further, various aspects may alternatively or optionally include steps related to frequency hopping generating random frequency hops on a narrow band transmitted signal.

Further yet, various aspects may alternatively or optionally include steps related to collision avoidance such as transmitting, via a first in vivo transmitter and a second in vivo transmitter, at different frequencies; modulating a duty cycle; retransmitting randomly; and spreading across a frequency spectrum. Modulating a duty cycle may include dithering the duty cycle and spreading among frequencies. Transmitting at different frequencies may comprise providing multiple band pass filtering by different devices wherein respective signals associated with different frequencies are filtered by respective band pass fillers.

Articles

Various aspects may include an article, comprising, for example, a storage medium having instructions, that when executed by a computing platform, result in execution of a method of providing transbody communications employing communication channels. The method, for example, may comprise various steps/combinations of steps such as transmitting, via an in vivo transmitter, an encoded signal; facilitating, via a transbody functionality module, communication of the signal; and receiving, via a receiver, the encoded signal. Various other steps are illustrated heretofore.

Additional System Aspects

In certain aspects, the receivers are part of a body associated system or network of sensors, receivers, and optionally other devices, both internal and external, which provide a variety of different types of information that is ultimately collected and processed by a processor, such as an external processor, which then can provide contextual data about a patient as output. For example that sensor may be a member of an in-body network of devices which can provide an output that includes data about pill ingestion, one or more physiological sensed parameters, implantable device operation, etc., to an external collector of the data. The external collector, e.g., in the form of a health care network server, etc., of the data then combines this receiver provided data with additional relevant data about the patient, e.g., weight, weather, medical record data, etc., and may process this disparate data to provide highly specific and contextual patient specific data.

Systems of the subject invention include, in certain aspects, a receiver and one or more pharma-informatics enabled active agent containing compositions. The pharma-informatics enabled pharmaceutical composition is an active agent-containing composition having an identifier stably associated therewith. In certain aspects, the compositions are disrupted upon administration to a subject. As such, in certain aspects, the compositions are physically broken, e.g., dissolved, degraded, eroded, etc., following delivery to a body, e.g., via ingestion, injection, etc. The compositions of these aspects are distinguished from devices that are configured to be ingested and survive transit through the gastrointestinal tract substantially, if not completely, intact. The compositions include an identifier and an active agent/carrier component, where both of these components are present in a pharmaceutically acceptable vehicle.

The identifiers of the compositions may vary depending on the particular aspect and intended application of the composition so long as they are activated (i.e., turned on) upon contact with a target physiological location, e.g., stomach. As such, the identifier may be an identifier that emits a signal when it contacts a target body (i.e., physiological) site. In addition or alternatively, the identifier may be an identifier that emits a signal when interrogated after it has been activated. The identifier may be any component or device that is capable of providing a detectable signal following activation, e.g., upon contact with the target site. In certain aspects, the identifier emits a signal once the composition comes into contact with a physiological target site, e.g., as summarized above. For example, a patient may ingest a pill that, upon contact with the stomach fluids, generates a detectable signal.

The compositions include an active agent/carrier component. By "active agent/carrier component" is meant a composition, which may be a solid or fluid (e.g., liquid), which has an amount of active agent, e.g., a dosage, present in a pharmaceutically acceptable carrier. The active agent/carrier component may be referred to as a "dosage formulation."

"Active agent" includes any compound or mixture of compounds which produces a physiological result, e.g., a beneficial or useful result, upon contact with a living organism, e.g., a mammal, such as a human. Active agents are distinguishable from such components as vehicles, carriers, diluents, lubricants, binders and other formulating aids, and encapsulating or otherwise protective components. The active agent may be any molecule, as well as binding portion or fragment thereof, that is capable of modulating a biological process in a living subject. In certain aspects, the active agent may be a substance used in the diagnosis, treatment, or prevention of a disease or as a component of a medication. In certain aspects, the active agent may be a chemical substance, such as a narcotic or hallucinogen, which affects the central nervous system and causes changes in behavior.

The active agent (i.e., drug) is capable of interacting with a target in a living subject. The target may be a number of different types of naturally occurring structures, where targets of interest include both intracellular and extracellular targets. Such targets may be proteins, phospholipids, nucleic acids and the like, where proteins are of particular interest. Specific proteinaceous targets of interest include, without limitation, enzymes, e.g. kinases, phosphatases, reductases, cyclooxygenases, proteases and the like, targets comprising domains involved in protein-protein interactions, such as the SH2, SH3, PTB and PDZ domains, structural proteins, e.g. actin, tubulin, etc., membrane receptors, immunoglobulins, e.g. IgE, cell adhesion receptors, such as integrins, etc, ion channels, transmembrane pumps, transcription factors, signaling proteins, and the like.

The active agent (i.e., drug) may include one or more functional groups necessary for structural interaction with the target, e.g., groups necessary for hydrophobic, hydrophilic, electrostatic or even covalent interactions, depending on the particular drug and its intended target. Where the target is a protein, the drug moiety may include functional groups necessary for structural interaction with proteins, such as hydrogen bonding, hydrophobic-hydrophobic interactions, electrostatic interactions, etc., and may include at least an amine, amide, sulfhydryl, carbonyl, hydroxyl or carboxyl group, such as at least two of the functional chemical groups.

Drugs of interest may include cyclical carbon or heterocyclic structures and/or aromatic or polyaromatic structures substituted with one or more of the above functional groups. Also of interest as drug moieties are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The drugs may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the drug may be obtained from a library of naturally occurring or synthetic molecules, including a library of compounds produced through combinatorial means, i.e., a compound diversity combinatorial library. When obtained from such libraries, the drug moiety employed will have demonstrated some desirable activity in an appropriate screening assay for the activity. Combinatorial libraries, as well as methods for producing and screening such libraries, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; etc.

As summarized above, the compositions of the invention further include a pharmaceutically acceptable vehicle (i.e., carrier). Common carriers and excipients, such as corn starch or gelatin, lactose, dextrose, sucrose, microcrystalline cellulose, kaolin, mannitol, dicalcium phosphate, sodium chloride, and alginic acid are of interest. Disintegrators commonly used in the formulations of the invention include croscarmellose, microcrystalline cellulose, corn starch, sodium starch glycolate and alginic acid.

Further details about aspects of pharma-informatics enabled pharmaceutical compositions may be found in pending PCT application PCT/US2006/16370 titled "Pharma-Informatics System" and filed on Apr. 28, 2006; as well as U.S. Provisional Application Ser. Nos. 60/807,060 titled "Acoustic Pharma-Informatics System" filed on Jul. 11, 2006; 60/862,925 titled "Controlled Activation Pharma-Informatics System," filed on Oct. 25, 2006; and 60/866,581 titled "In-Vivo Transmission Decoder," filed on Nov. 21, 2006; the disclosures of which are herein incorporated by reference.

In certain aspects the systems include an external device which is distinct from the receiver (which may be implanted or topically applied in certain aspects), where this external device provides a number of functionalities. Such an apparatus can include the capacity to provide feedback and appropriate clinical regulation to the patient. Such a device can take any of a number of forms. By example, the device can be configured to sit on the bed next to the patient, e.g., a bedside monitor. Other formats include, but are not limited to, PDAs, smart phones, home computers, etc. The device can read out the information described in more detail in other sections of the subject patent application, both from pharmaceutical ingestion reporting and from physiological sensing devices, such as is produced internally by a pacemaker device or a dedicated implant for detection of the pill. The purpose of the external apparatus is to get the data out of the patient and into an external device. One feature of the external apparatus is its ability to provide pharmacologic and physiologic information in a form that can be transmitted through a transmission medium, such as a telephone line, to a remote location such as a clinician or to a central monitoring agency.

Systems of the invention enable a dynamic feedback and treatment loop of tracking medication timing and levels, measuring the response to therapy, and recommending altered dosing based on the physiology and molecular profiles of individual patients. For example, a symptomatic heart failure patient takes multiple drugs daily, primarily with the goal of reducing the heart's workload and improving patient quality of life. Mainstays of therapy include angiotensin converting enzyme (ACE) inhibitors, β-blockers and diuretics. For pharmaceutical therapy to be effective, it is vital that patients adhere to their prescribed regimen, taking the required dose at the appropriate time. Multiple studies in the clinical literature demonstrate that more than 50% of Class II and III heart failure patients are not receiving guideline-recommended therapy, and, of those who are titrated appropriately, only 40-60% adhere to the regimen. With the subject systems, heart failure patients can be monitored for patient adherence to therapy, and adherence performance can be linked to key physiologic measurements, to facilitate the optimization of therapy by physicians.

In certain aspects, the systems of the invention may be employed to obtain an aggregate of information that includes sensor data and administration data. For example, one can combine the heart rate, the respiration rate, multi-axis acceleration data, something about the fluid status, and something about temperature, and derive indices that will inform about the total activity of the subject, that can be used to generate a physiological index, such as an activity index. For instance, when there is a rise in temperature, heart rate goes up a bit, and respiration speeds up, which may be employed as an indication that the person is being active. By calibrating this, the amount of calories the person is burning at that instant could be determined. In another example, a particular rhythmic set of pulses or multi-axis acceleration data can indicate that a person is walking up a set of stairs, and from that one can infer how much energy they are using. In another aspect, body fat measurement (e.g. from impedance data) could be combined with an activity index generated from a combination of measured biomarkers to generate a physiological index useful for management of a weight loss or cardiovascular health program. This information can be combined with cardiac performance indicators to get a good picture of overall health, which can be combined with pharmaceutical therapy administration data. In another aspect, one might find for example that a particular pharmaceutical correlates with a small increase in body temperature, or a change in the electrocardiogram. One can develop a pharmacodynamic model for the metabolism of the drug, and use the information from the receiver to essentially fit the free parameters in that model to give much more accurate estimation of the levels actually present in the serum of the subject. This information could be fed back to dosing regimes. In another aspect, one can combine information from a sensor that measures uterine contractions (e.g. with a strain gauge) and that also monitors fetal heart rate, for use as a high-risk pregnancy monitor.

In certain aspects, the subject specific information that is collected using the systems of the invention may be transmitted to a location where it is combined with data from one or more additional individuals to provide a collection of data which is a composite of data collected from 2 or more, e.g., 5 or more, 10 or more, 25 or more, 50 or more, 100 or more, 1000 or more, etc., individuals. The composite data can then be manipulated, e.g., categorized according to different criteria, and made available to one or more different types of groups, e.g., patient groups, health care practitioner groups, etc., where the manipulation of data may be such as to limit the access of any given group to the type of data that group can access. For example, data can be collected from 100 different individuals that are suffering from the same condition and taking the same medication. The data can be processed and employed to develop easy to follow displays regarding patient compliance with a pharmaceutical dosage regimen and general health. Patient members of the group can access this information and see how their compliance matches with other patient members of the group, and whether they are enjoying the benefits that others are experiencing. In yet another aspect, doctors can also be granted access to a manipulation of the composite data to see how their patients are matching up with patients of other doctors, and obtain useful information on how real patients respond to a given therapeutic treatment regimen. Additional functionalities can be provided to the groups given access to the composite data, where such functionalities may include, but are not limited to: ability to annotate data, chat functionalities, security privileges, etc.

Computer Readable Media & Programming

In certain aspects, the system further includes an element for storing data, i.e., a data storage element, where this element is present on an external device, such as a bedside monitor, PDA, smart phone, etc. Typically, the data storage element is a computer readable medium. The term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

The invention also provides computer executable instructions (i.e., programming) for performing the above methods. The computer executable instructions are present on a computer readable medium. Accordingly, the invention provides a computer readable medium containing programming for use in detecting and processing a signal generated by a composition of the invention, e.g., as reviewed above.

As such, in certain aspects the systems include one or more of: a data storage element, a data processing element, a data display element, data transmission element, a notification mechanism, and a user interface. These additional elements may be incorporated into the receiver and/or present on an external device, e.g., a device configured for processing data and making decisions, forwarding data to a remote location which provides such activities, etc.

The above described systems are reviewed in terms of communication between an identifier on a pharmaceutical composition and a receiver. However, the systems are not so limited. In a broader sense, the systems are composed of two or more different modules that communicate with each other, e.g., using the transmitter/receiver functionalities as reviewed above, e.g., using the monopole transmitter (e.g., antenna) structures as described above. As such, the above identifier elements may be incorporated into any of a plurality of different devices, e.g., to provide a communications system between two self-powered devices in the body, where the self-powered devices may be sensors, data receivers and storage elements, effectors, etc. In an exemplary system, one of these devices may be a sensor and the other may be a communication hub for communication to the outside world. This inventive aspect may take a number of forms. There can be many sensors, many senders and one receiver. They can be transceivers so both of these can take turns sending and receiving according to known communication protocols. In certain aspects, the means of communication between the two or more individual devices is the mono polar system, e.g., as described above. In these aspects, each of these senders may be configured to take turns sending a high frequency signal into the body using a monopole pulling charge into and out of the body which is a large capacitor and a conductor. The receiver, a monopole receiver is detecting at that frequency the charge going into and out of the body and decoding an encrypted signal such as an amplitude modulated signal or frequency modulated signal. This aspect of the present invention has broad uses. For example, multiple sensors can be placed and implanted on various parts of the body that measure position or acceleration. Without having wires connecting to a central hub, they can communicate that information through a communication medium.

In the methods of the subject invention in which the in vivo transmitter is a pharma-informatics enabled composition, an effective amount of a composition of the invention is administered to a subject in need of the active agent present in the composition, where "effective amount" means a dosage sufficient to produce the desired result, e.g. an improvement in a disease condition or the symptoms associated therewith, the accomplishment of a desired physiological change, etc. The amount that is administered may also be viewed as a therapeutically effective amount. A "therapeutically effective amount" means the amount that, when administered to a subject for treating a disease, is sufficient to effect treatment for that disease.

The composition may be administered to the subject using any convenient means capable of producing the desired result, where the administration route depends, at least in part, on the particular format of the composition, e.g., as reviewed above. As reviewed above, the compositions can be formatted into a variety of formulations for therapeutic administration, including but not limited to solid, semi solid or liquid, such as tablets, capsules, powders, granules, ointments, solutions, suppositories and injections. As such, administration of the compositions can be achieved in various ways, including, but not limited to: oral, buccal, rectal, parenteral, intraperitoneal, intradermal, transdermal, intracheal, etc., administration. In pharmaceutical dosage forms, a given composition may be administered alone or in combination with other pharmaceutically active compounds, e.g., which may also be compositions having signal generation elements stably associated therewith.

The subject methods find use in the treatment of a variety of different conditions, including disease conditions. The specific disease conditions treatable by with the subject compositions are as varied as the types of active agents that can be present in the subject compositions. Thus, disease conditions include, but are not limited to: cardiovascular diseases, cellular proliferative diseases, such as neoplastic diseases, autoimmune diseases, hormonal abnormality diseases, infectious diseases, pain management, and the like.

By treatment is meant at least an amelioration of the symptoms associated with the disease condition afflicting the subject, where amelioration is used in a broad sense to refer to at least a reduction in the magnitude of a parameter, e.g. symptom, associated with the pathological condition being treated. As such, treatment also includes situations where the pathological condition, or at least symptoms associated therewith, are completely inhibited, e.g. prevented from happening, or stopped, e.g. terminated, such that the subject no longer suffers from the pathological condition, or at least the symptoms that characterize the pathological condition. Accordingly, "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). For the purposes of this invention, a "disease" includes pain.

A variety of subjects are treatable according to the present methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In representative aspects, the subjects will be humans.

In certain aspects, the subject methods, as described above, are methods of managing a disease condition, e.g., over an extended period of time, such as 1 week or longer, 1 month or longer, 6 months or longer, 1 year or longer, 2 years or longer, 5 years or longer, etc. The subject methods may be employed in conjunction with one or more additional disease management protocols, e.g., electrostimulation based protocols in cardiovascular disease management, such as pacing protocols, cardiac resynchronization protocols, etc; lifestyle, such a diet and/or exercise regimens for a variety of different disease conditions; etc.

In certain aspects, the methods include modulating a therapeutic regimen based data obtained from the compositions. For example, data may be obtained which includes information about patient compliance with a prescribed therapeutic regimen. This data, with or without additional physiological data, e.g., obtained using one or more sensors, such as the sensor devices described above, may be employed, e.g., with appropriate decision tools as desired, to make determinations of whether a given treatment regimen should be maintained or modified in some way, e.g., by modification of a medication regimen and/or implant activity regimen. As such, methods of invention include methods in which a therapeutic regimen is modified based on signals obtained from the composition(s).

In certain aspects, also provided are methods of determining the history of a composition of the invention, where the composition includes an active agent, an identifier element and a pharmaceutically acceptable carrier. In certain aspects where the identifier emits a signal in response to an interrogation, the identifier is interrogate, e.g., by a wand or other suitable interrogation device, to obtain a signal. The obtained signal is then employed to determine historical information about the composition, e.g., source, chain of custody, etc.

In yet other aspects where the identifier is one that survives digestion, the methods generally include obtaining the signal generation element of the composition, e.g., by retrieving it from a subject that has ingested the composition, and then determining the history of the composition from obtained signal generation element. For example, where the signal generation element includes an engraved identifier, e.g., barcode or other type of identifier, the engraved identifier may be retrieved from a subject that has ingested the composition and then read to identify at least some aspect of the history of the composition, such as last known purchaser, additional purchasers in the chain of custody of the composition, manufacturer, handling history, etc. In certain aspects, this determining step may include accessing a database or analogous compilation of stored history for the composition.

Utility

Medical aspects of the present invention provide the clinician an important new tool in their therapeutic armamentarium: automatic detection and identification of pharmaceutical agents actually delivered into the body. The applications of this new information device and system are multi-fold. Applications include, but are not limited to: (1) monitoring patient compliance with prescribed therapeutic regimens; (2) tailoring therapeutic regimens based on patient compliance; (3) monitoring patient compliance in clinical trials; (4) monitoring usage of controlled substances; and the like. Each of these different illustrative applications is reviewed in greater detail below in copending PCT Application Serial No. PCT/US2006/016370; the disclosure of which is herein incorporated by reference. Additional applications in which the subject receivers find use include, but are not limited to: U.S. provisional Application Ser. Nos. 60/887,780 titled "Receivers For Pharma-Informatics Systems," and filed on Feb. 1, 2007; 60/956,694 titled "Personal Health Receivers," and filed on Aug. 18, 2007 and 60/949,223 titled "Ingestible Event Marker," and filed on Jul. 11, 2007, the disclosures of which applications are incorporated herein by reference.

Kits

Also provided are kits for practicing the subject methods. Kits may include one or more receivers of the invention, as described above. In addition, the kits may include one or more dosage compositions, e.g., pharma-informatics enabled dosage compositions. The dosage amount of the one or more pharmacological agents provided in a kit may be sufficient for a single application or for multiple applications. Accordingly, in certain aspects of the subject kits a single dosage amount of a pharmacological agent is present and in certain other aspects multiple dosage amounts of a pharmacological agent may be present in a kit. In those aspects having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit is dictated by the particular pharmacological agent employed, as describe above, e.g., the particular form of the agent such as whether the pharmacological agent is formulated into preparations in solid, semi solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperitoneal, intradermal, transdermal, intracheal, etc. Accordingly, certain systems may include a suppository applicator, syringe, I. V. bag and tubing, electrode, etc.

In certain aspects, the kits may also include an external monitor device, e.g., as described above, which may provide for communication with a remote location, e.g., a doctor's office, a central facility etc., which obtains and processes data obtained about the usage of the composition.

In certain aspects, the kits may include a smart parenteral delivery system that provides specific identification and detection of parenteral beneficial agents or beneficial agents taken into the body through other methods, for example, through the use of a syringe, inhaler, or other device that administers medicine, such as described in application Ser. No. 60/819,750; the disclosure of which is herein incorporated by reference.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other aspects, the instructions are present as an electronic storage data file present on a suitable computer readable storage medium, e.g. CD-ROM, diskette, etc. In yet other aspects, the actual instructions are not present in the kit, but means for obtaining the instructions from a remote source, e.g. via the internet, are provided. An example of this aspect is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many aspects of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is to be understood that this invention is not limited to particular aspects described, as such may vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention.

The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which may be readily separated from or combined with the features of any of the other several aspects without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

The invention claimed is:

1. A communication system characterized by an uncertainty in a first frequency of a signal from an ingestible transmitter, the system comprising:
   the ingestible transmitter comprising:
      a silicon chip comprising:
         an integrated circuit;
         a first surface coated with a first digestible material; and
         a second surface coated with a second digestible material, wherein the first and second digestible materials power the integrated circuit while being digested; and
      an oscillator comprising a conductor, a resistor, a capacitor, and a transistor, the oscillator configured to produce the first frequency that varies within a range of plus or minus 1% from a target frequency when the oscillator is ingested;
   wherein the ingestible transmitter is configured to transmit the signal, the signal comprising, according to a communication protocol, a beacon channel at the first frequency and a message channel at a second frequency that is related to the first frequency by a first fixed ratio; and a receiver comprising:
      one or more electrodes configured to detect the signal, and
      a processor configured to:
         determine the first frequency associated with the signal;
         determine the second frequency associated with the signal; and compute a first computed ratio between the first detected frequency and the second detected frequency.

2. The system of claim 1, wherein the oscillator is a silicon oscillator.

3. The system of claim 1, wherein the signal is a conductive signal that is transmitted by the ingestible transmitter to the receiver via body fluids.

4. The system of claim 1 wherein the ingestible transmitter is further configured to transmit the signal that further comprises, according to the communication protocol:
a first arrival time of the first frequency;
a second arrival time of the second frequency; and
a second fixed ratio comparing the first arrival time to the second arrival time.

5. The system of claim 4, wherein the processor is further configured to:
determine the first arrival time of the first frequency;
determine the second arrival time of the second frequency; and
compute a second computed ratio of the first arrival time to the second arrival time.

6. The system of claim 5, wherein the processor is further configured to:
compare the computed first ratio to the first fixed ratio;
compare the computed second ratio to the fixed second ratio; and
compute an estimate of the first and second frequencies using the comparisons of the computed and fixed ratios.

7. A method of a communication system characterized by a large uncertainty in a carrier frequency from an ingestible transmitter, the system comprising the ingestible transmitter and a receiver, the method comprising:
transmitting a conductive signal through a living body, by the ingestible transmitter after it has been ingested, the signal comprising, according to a communication protocol:
a beacon channel at a first frequency that varies within a range of plus or minus 1% from a target frequency during transmission of the signal, wherein the variance is uncertain to the receiver; and
a message channel at a second frequency that is related to the first frequency by a first fixed ratio;
determining, by the receiver, the first frequency;
determining, by the receiver, the second frequency; and
computing, by the receiver, a first computed ratio between the first determined frequency and the second determined frequency.

8. The method of claim 7, wherein the ingestible transmitter transmits the signal using a silicon oscillator.

9. The method of claim 8, wherein the silicon oscillator comprises a conductor, a resistor, a capacitor, and a transistor.

10. The method of claim 7, wherein the conductive signal is transmitted by the ingestible transmitter to the receiver via body fluids.

11. The method of claim 7, wherein transmitting the signal, by the ingestible transmitter, further comprises transmitting, according to the communication protocol:
a first arrival time of the first frequency;
a second arrival time of the second frequency; and
a second fixed ratio comparing the first arrival time to the second arrival time.

12. The method of claim 11, further comprising:
determining, by the receiver, a first arrival time of the first frequency;
determining, by the receiver, a second arrival time of the second frequency; and
computing, by the receiver, a second computed ratio of the first the arrival time to the second arrival time.

13. The method of claim 12, further comprising:
comparing, by the receiver, the computed first ratio to the first fixed ratio;
comparing, by the receiver, the computed second ratio to the fixed second ratio; and
computing, by the receiver, an estimate of the first and second frequencies using the comparisons of the computed and fixed ratios.

14. A method of a receiver of a communication system characterized by a large uncertainty in a carrier frequency from an ingestible transmitter, the method comprising:
receiving a conductive signal through a living body, the signal comprising, according to a communication protocol:
a beacon channel at a first frequency that varies within a range of plus or minus 1% from a target frequency during transmission of the signal, wherein the variance is uncertain to the receiver; and
a message channel at a second frequency that is related to the first frequency by a first fixed ratio;
determining the first frequency;
determining the second frequency; and
computing a first computed ratio between the first determined frequency and the second determined frequency.

15. The method of claim 14, wherein the signal is transmitted using a silicon oscillator.

16. The method of claim 15, wherein the silicon oscillator comprises a conductor, a resistor, a capacitor, and a transistor.

17. The method of claim 14, wherein the conductive signal is transmitted by the ingestible transmitter to the receiver via body fluids.

18. The method of claim 14, wherein receiving the signal further comprises receiving, according to the communication protocol:
a first arrival time of the first frequency;
a second arrival time of the second frequency; and
a second fixed ratio comparing the first arrival time to the second arrival time.

19. The method of claim 18, further comprising:
determining the first arrival time of the first frequency;
determining the second arrival time of the second frequency; and
computing a second computed ratio of the first the arrival time to the second arrival time.

20. The method of claim 19, further comprising:
comparing the computed first ratio to the first fixed ratio;
comparing the computed second ratio to the fixed second ratio; and
computing an estimate of the first and second frequencies using the comparisons of the computed and fixed ratios.

* * * * *